US006919177B2

(12) United States Patent
Rothschild et al.

(10) Patent No.: US 6,919,177 B2
(45) Date of Patent: Jul. 19, 2005

(54) PRKAG3 ALLELES AND USE OF THE SAME AS GENETIC MARKERS FOR REPRODUCTIVE AND MEAT QUALITY TRAITS

(75) Inventors: Max F. Rothschild, Ames, IA (US); Daniel C. Ciobanu, Ames, IA (US); Massoud Malek, Ames, IA (US); Graham Plastow, Cambridge (GB)

(73) Assignee: Iowa State University Research Foundation, Inc., Ames, IA (US)

( * ) Notice: Subject to any disclaimer, the term of this patent is extended or adjusted under 35 U.S.C. 154(b) by 52 days.

(21) Appl. No.: 09/950,022

(22) Filed: Sep. 10, 2001

(65) Prior Publication Data

US 2003/0017470 A1 Jan. 23, 2003

Related U.S. Application Data

(60) Provisional application No. 60/231,045, filed on Sep. 8, 2000, provisional application No. 60/260,239, filed on Jan. 8, 2001, and provisional application No. 60/299,111, filed on Jun. 18, 2001.

(51) Int. Cl.[7] ................................................ C12Q 1/68
(52) U.S. Cl. .......................................... 435/6; 435/91.2
(58) Field of Search .................... 435/6, 91.2; 536/23.1

(56) References Cited

FOREIGN PATENT DOCUMENTS

| WO | WO 97/35878 A | 10/1997 |
| WO | WO 99/15639 A | 4/1999 |
| WO | WO 99/52942 | * 10/1999 |
| WO | WO 00/42218 A | 7/2000 |
| WO | WO 01/20003 | 3/2001 |

OTHER PUBLICATIONS

Lundstrom et al. (2001J. Dairy Science, vol. 1, Suppl. 1, p. 255, abstract No. 1052).*
Hacker et al. (Gut, 1997, vol. 40, pp. 623–627).*
Pennisi, Science, 281 (5384):1787–1789.*
Vincek et al. (Mammalian Genome 5, 376–379 (1994)).*
Juppner (Bone vol. 17, No. 2, Supplement, Aug. 1995: 39S–42S).*
Milan, D., et al., "A Mutation in PRKAG3 Associated with Excess Glycogen Content in Pig Skeletal Muscle", *Science* 288:1248–1251 (May 19, 2000).
Rothschild et al., "Investigation of the retinol–binding protein 4 (RBP4) gene as a candidate gene for increased litter size in pigs", Mammalian Genome: Official Journal of the International Mammalian Genome Society, US Jan. 2000, vol. 11(1):01–2001, pp. 75–77, XP002224845, ISSN:0938–8990.

* cited by examiner

*Primary Examiner*—Juliet C. Switzer
(74) *Attorney, Agent, or Firm*—McKee, Voorhees & Sease, P.L.C.

(57) ABSTRACT

Disclosed herein are genetic markers for animal meat quality and reproductive efficiency, methods for identifying such markers, and methods of screening animals to determine those more likely to produce larger litters and/or better meat quality and preferably selecting those animals for future breeding purposes. The markers are based upon the presence or absence of certain polymorphisms in the PRKAG3 gene.

23 Claims, 6 Drawing Sheets

```
  1  ATGAGCTTCCTAGAGCAAGGAGAGAGCCGTTCATGGCCATCCCGAGCTGTAACCACCAGCTCAGAAAGAA
     M  S  F  L  E  Q  G  E  S  R  S  W  P  S  R  A  V  T  T  S  S  E  R
                              30
                              AcC
                              T
 71  GCCATGGGGACCAGGGGAaCAAGGCCTCTAGATGGACAAGGCAGGAGGATGTAGAGGAAGGGGGGCCTCC
     S  H  G  D  Q  G  N  K  A  S  R  W  T  R  Q  E  D  V  E  E  G  P  P
                     52
                     aGT
                     S
141  GGGCCCGAGGGAAgGTCCCCAGTCCAGGCCAGTTGCTGAGTCCACCGGGCAGGAGGCCACATTCCCCAAG
     G  P  R  E  G  P  Q  S  R  P  V  A  E  S  T  G  Q  E  A  T  F  P  K
211  GCCACACCCTTGGCCCAAGCCGCTCCCTTGGCCGAGGTGGACAACCCCCCAACAGAGCGGGACATCCTCC
     A  T  P  L  A  Q  A  A  P  L  A  E  V  D  N  P  P  T  E  R  D  I  L
281  CCTCTGACTGTGCAGCCTCAGCCTCCGACTCCAACACAGACCATCTGGATCTGGGCATAGAGTTCTCAGC
     P  S  D  C  A  A  S  A  S  D  S  N  T  D  H  L  D  L  G  I  E  F  S  A
351  CTCGGCGGCGTCGGGGGATGAGCTTGGGCTGGTGGAAGAGAAGCCAGCCCCGTGCCCATCCCCAGAGGTG
        S  A  A  S  G  D  E  L  G  L  V  E  E  K  P  A  P  C  P  S  P  E  V
421  CTGTTACCCAGGCTGGGCTGGGATGATGAGCTGCAGAAGCCGGGGCCCAGGTCTACATGCACTTCATGC
     L  L  P  R  L  G  W  D  D  E  L  Q  K  P  G  A  Q  V  Y  M  H  F  M
491  AGGAGCACACCTGCTACGATGCCATGGCGACCAGCTCCAAACTGGTCATCTTCGACACCATGCTGGAGAT
     Q  E  H  T  C  Y  D  A  M  A  T  S  S  K  L  V  I  F  D  T  M  L  E  I
                                                        199200
                                                        aTCCaA
                                                        I  Q
561  CAAGAAGGCCTTCTTTGCCCTGGTGGCCAACGGCgTCCgAGCGGCACCTTTGTGGGACAGCAAGAAGCAG
        K  K  A  F  F  A  L  V  A  N  G  V  R  A  A  P  L  W  D  S  K  K  Q
631  AGCTTCGTGGGGATGCTGACCATCACAGACTTCATCTTGGTGCTGCACCGCTATTACAGGTCCCCCCTGG
        S  F  V  G  M  L  T  I  T  D  F  I  L  V  L  H  R  Y  Y  R  S  P  L
701  TCCAGATCTACGAGATTGAAGAACATAAGATTGAGACCTGGAGGGAGATCTACCTTCAAGGCTGCTTCAA
     V  Q  I  Y  E  I  E  E  H  K  I  E  T  W  R  E  I  Y  L  Q  G  C  F  K
771  GCCTCTGGTCTCCATCTCTCCCAATGACAGCCTGTTCGAAGCTGTCTACGCCCTCATCAAGAACCGGATC
        P  L  V  S  I  S  P  N  D  S  L  F  E  A  V  Y  A  L  I  K  N  R  I
841  CACCGCCTGCCGGTCCTGGACCCTGTCTCCGGGGCTGTGCTCCACATCCTCACACATAAGCGGCTTCTA
     H  R  L  P  V  L  D  P  V  S  G  A  V  L  H  I  L  T  H  K  R  L  L
911  AGTTCCTGCACATCTTTGGCACCCTGCTGCCCCGGCCCTCCTTCCTCTACCGCACCATCCAAGATTTGGG
     K  F  L  H  I  F  G  T  L  L  P  R  P  S  F  L  Y  R  T  I  Q  D  L  G
981  CATCGGCACATTCCGAGACTTGGCCGTGGTGCTGGAAACGGCGCCCATCCTGACCGCACTGGACATCTTC
        I  G  T  F  R  D  L  A  V  V  L  E  T  A  P  I  L  T  A  L  D  I  F
051  GTGGACCGGCGTGTGTCTGCGCTGCCTGTGGTCAACGAAACTGGACAGGTAGTGGGCCTCTACTCTCGCT
        V  D  R  R  V  S  A  L  P  V  V  N  E  T  G  Q  V  V  G  L  Y  S  R
1121 TTGATGTGATCCACCTGGCTGCCCAACAAACATACAACCACCTGGACATGAATGTGGGAGAAGCCCTGAG
     F  D  V  I  H  L  A  A  Q  Q  T  Y  N  H  L  D  M  N  V  G  E  A  L  R
1191 GCAGCGGACACTGTGTCTGGAAGGCGTCCTTTCCTGCCAGCCCCACGAGACCTTGGGGGAAGTCATTGAC
     Q  R  T  L  C  L  E  G  V  L  S  C  Q  P  H  E  T  L  G  E  V  I  D
1261 CGGATTGTCCGGGAACAGGTGCACCGCCTGGTGCTCGTGGATGAGACCCAGCACCTTCTGGGCGTGGTGT
        R  I  V  R  E  Q  V  H  R  L  V  L  V  D  E  T  Q  H  L  L  G  V  V
1331 CCCTCTCTGACATCCTTCAGGCTCTGGTGCTCAGCCCTGCTGGAATTGATGCCCTCGGGGCCTGAGAACC
        S  L  S  D  I  L  Q  A  L  V  L  S  P  A  G  I  D  A  L  G  A  *
1401 TTGGAACCTTTGCTCTCAGGCCACCTGGCACACCTGGAAGCCAGTGAAGGGAGCCGTGGACTCAGCTCTC
1471 ACTTCCCCTCAGCCCCACTTGCTGGTCTGGCTCTTGTTCAGGTAGGCTCCGCCCGGGCCCCTGGCCTCA
1541 GCATCAGCCCCTCAGTCTCCCTGGGCACCCAGATCTCAGACTGGGGCACCCTGAAGATGGGAGTGGCCCA
1611 GCTTATAGCTGAGCAGCCTTGTGAAATCTACCAGCATCAAGACTCACTGTGGGACCACTGCTTTGTCCCA
1681 TTCTCAGCTGAAATGATGGAGGGCCTCATAAGAGGGGTGGACAGGGCCTGGAGTAGAGGCCAGATCAGTG
1751 ACGTGCCTTCAGGACCTCCGGGGAGTTAGAGCTGCCCTCTCTCAGTTCAGTTCCCCCCTGCTGAGAATGT
1821 CCCTGGAAGGAAGCCAGTTAATAAACCTTGGTTGGATGGAATTTGGAGAGTCG
```

*Fig.1*

GAAACTCTTCTCCCCACA*GACTCCCTCCTGGAGCAGCCTCGGGGGACCTAAGC*
*ATCAAG*GTAGGTGGGGCTGCCCCTGCTCGCGGGCCCAGGCTCTTCTCCCACCT
CCTTTTCTTCCACGTCTTCAGGACCCCAATCTCCCCCACTCCACTCGCCTGGCT
CTTGTCTTCCTCTCCTTTGCCTTCTTTGTTCCGCTTTGTTTCTTCTTCCTCCCTCT
CCCTCACCTCCTCCCTCTTTCAAAAGAGTAGAGGGGGCATCTATAGAGTCTGG
AGATTGGGACTCTCTTGACTTTCTCGCTTACTAGCTGTGTGATTTGTGGC
AAATTGCTTCACCTCTCTGAGCTCAGGTCTCTCGTTAGTAAAACAGGGCT
GATAGCCATGCCCTTCGGATAAGATTGCCGTGAGGGTTGAATGAGAAATT
TGTTGGAGGACAAGCCCTTTGAAGCTTCCCAATATTAAATATTTTTATTT
ATTTATTTATTTTTTGTCTTTTTGCTATTCCTTTGGGCCGCTCCCACGGC
ATATGGAGGTTCCCAGGCTAGGGGTCGAATCGGAGCTGTAGCCACTGGCC
TACGCCAGAGCCACAGCAACGCGGGATCCGAGCCGCATCTGCAACCTACA
CCACAGCTCACGGCAACGCCGGATCGTTAACCCACTGAGCAGGGCAGGC
ACCGAACCTGCAACCTCATGGTTCCTAGTGGGATTCGTTAACCACTGCGC
CACGACGGGAACTCCCCAATATTAAATATTATTAGTAACATTTTAAT
GGAATTTATTGTGTTACTCCCCATTAACCAAACAGGTCCCATTCTCCCTT
GCAGAG*ATGAGCTTCCTAGAGCAAGGAGAGAGCCGTTCATGGCCATCCCG*
*AGCTGTGACCACCAGCTCAGAAAGAAGCCATGGGGACCAGGGGACCAAGG*
*CCTCTAGATGGACAAGGCAGGAGGATRTAGAGGAAGGGGGGCCTCCGGGC*
*CCGAGGGAAR*GTGAGTTCAAGGCCAGTTCTGGGGAGCTGGGACTGGGGGC
AGTGGGCAGTCCTCAAACCTGGGGCCCGTCTCTGGTCTGGTCCCTCCATA
ACACAGGCACATAACATCATGCAGCC

*Fig. 2A*

GAAACTCTTCTCCCCACA*GACTCCCTCCTGGAGCAGCCTCGGGGGACCTA*
*AGCATCAAG*GTAGGTGGGGCTGCCCCTGCTCGCGGGCCCAGGCTCTTCTC
CCACCTCCTTTTCTTCCACGTCTTCAGGACCCCAATCTCCCCCACTCCAC
TCGCCTGGCTCTTGTCTTCCTCTCCTTTGCCTTCTTTGTTCCGCTTTGTT
TCTTCTTCCTCCCTCTCCCTCACCTCCTCCCTCTTTCAAAAGAGTAGAGG
GGGCATCTATAGAGTCTGGAGATTGGGACTCTCTTGACTTTCTCGCTTAC
TAGCTGTGTGATTTGTGGCAAATTGCTTCACCTCTCTGAGCTCAGGTCTC
TCGTTAGTAAAACAGGGCTGATAGCCATGCCCTTCGGATAAGATTGCCGT
GAGGGTTGAATGAGAAATTTGTTGGAGGACAAGCCCTTTGAAGCTTCCCA
ATATTAAATATTATTATTAGTAACATTTTAATGGAATTTATTGTGTTACT
CCCCATTAACCAAACAGGTCCCATTCTCCCTTGCAGAG*ATGAGCTTCCTA*
*GAGCAAGGAGAGAGCCGTTCATGGCCATCCCGAGCTGTGACCACCAGCTC*
*AGAAAGAAGCCATGGGGACCAGGGGACCAAGGCCTCTAGATGGACAAGGC*
*AGGAGGATATAGAGGAAGGGGGGCCTCCGGGCCCGAGGGAAR*GTGAGTTC
AAGGCCAGTTCTGGGGAGCTGGGACTGGGGGCAGTGGGCAGTCCTCAAAC
CTGGGGCCCGTCTCTGGTCTGGTCCCTCCATAACACAGGCACATAACATC
ATGCAGCC

*Fig. 2B*

SEQUENCE LISTING

<160> NUMBER OF SEQ ID NOS: 21

<210> SEQ ID NO 1
<211> LENGTH: 1873
<212> TYPE: DNA
<213> ORGANISM: Sus scrofa
<220> FEATURE:
<221> NAME/KEY: CDS
<222> LOCATION: (1)..(1392)
<223> OTHER INFORMATION:

<400> SEQUENCE: 1

```
atg agc ttc cta gag caa gga gag agc cgt tca tgg cca tcc cga gct      48
Met Ser Phe Leu Glu Gln Gly Glu Ser Arg Ser Trp Pro Ser Arg Ala
1               5                   10                  15 gta acc acc agc tca gaa aga agc cat ggg gac cag ggg aac aag gcc      96
Val Thr Thr Ser Ser Glu Arg Ser His Gly Asp Gln Gly Asn Lys Ala
            20                  25                  30 tct aga tgg aca agg cag gag gat gta gag gaa ggg ggg cct ccg ggc     144
Ser Arg Trp Thr Arg Gln Glu Asp Val Glu Glu Gly Gly Pro Pro Gly
        35                  40                  45 ccg agg gaa ggt ccc cag tcc agg cca gtt gct gag tcc acc ggg cag     192
Pro Arg Glu Gly Pro Gln Ser Arg Pro Val Ala Glu Ser Thr Gly Gln
    50                  55                  60 gag gcc aca ttc ccc aag gcc aca ccc ttg gcc caa gcc gct ccc ttg     240
Glu Ala Thr Phe Pro Lys Ala Thr Pro Leu Ala Gln Ala Ala Pro Leu
65                  70                  75                  80 gcc gag gtg gac aac ccc cca aca gag cgg gac atc ctc ccc tct gac     288
Ala Glu Val Asp Asn Pro Pro Thr Glu Arg Asp Ile Leu Pro Ser Asp
                85                  90                  95 tgt gca gcc tca gcc tcc gac tcc aac aca gac cat ctg gat ctg ggc     336
Cys Ala Ala Ser Ala Ser Asp Ser Asn Thr Asp His Leu Asp Leu Gly
            100                 105                 110
```

```
                                                            -continued ata gag ttc tca gcc tcg gcg gcg tcg ggg gat gag ctt ggg ctg gtg    384
Ile Glu Phe Ser Ala Ser Ala Ala Ser Gly Asp Glu Leu Gly Leu Val
        115                 120                 125 gaa gag aag cca gcc ccg tgc cca tcc cca gag gtg ctg tta ccc agg    432
Glu Glu Lys Pro Ala Pro Cys Pro Ser Pro Glu Val Leu Leu Pro Arg
130                 135                 140 ctg ggc tgg gat gat gag ctg cag aag ccg ggg gcc cag gtc tac atg    480
Leu Gly Trp Asp Asp Glu Leu Gln Lys Pro Gly Ala Gln Val Tyr Met
145                 150                 155                 160 cac ttc atg cag gag cac acc tgc tac gat gcc atg gcg acc agc tcc    528
His Phe Met Gln Glu His Thr Cys Tyr Asp Ala Met Ala Thr Ser Ser
                165                 170                 175 aaa ctg gtc atc ttc gac acc atg ctg gag atc aag aag gcc ttc ttt    576
Lys Leu Val Ile Phe Asp Thr Met Leu Glu Ile Lys Lys Ala Phe Phe
        180                 185                 190 gcc ctg gtg gcc aac ggc gtc cga gcg gca cct ttg tgg gac agc aag    624
Ala Leu Val Ala Asn Gly Val Arg Ala Ala Pro Leu Trp Asp Ser Lys
    195                 200                 205 aag cag agc ttc gtg ggg atg ctg acc atc aca gac ttc atc ttg gtg    672
Lys Gln Ser Phe Val Gly Met Leu Thr Ile Thr Asp Phe Ile Leu Val
210                 215                 220 ctg cac cgc tat tac agg tcc ccc ctg gtc cag atc tac gag att gaa    720
Leu His Arg Tyr Tyr Arg Ser Pro Leu Val Gln Ile Tyr Glu Ile Glu
225                 230                 235                 240 gaa cat aag att gag acc tgg agg gag atc tac ctt caa ggc tgc ttc    768
Glu His Lys Ile Glu Thr Trp Arg Glu Ile Tyr Leu Gln Gly Cys Phe
                245                 250                 255 aag cct ctg gtc tcc atc tct ccc aat gac agc ctg ttc gaa gct gtc    816
Lys Pro Leu Val Ser Ile Ser Pro Asn Asp Ser Leu Phe Glu Ala Val
        260                 265                 270 tac gcc ctc atc aag aac cgg atc cac cgc ctg ccg gtc ctg gac cct    864
Tyr Ala Leu Ile Lys Asn Arg Ile His Arg Leu Pro Val Leu Asp Pro
    275                 280                 285 gtc tcc ggg gct gtg ctc cac atc ctc aca cat aag cgg ctt ctc aag    912
Val Ser Gly Ala Val Leu His Ile Leu Thr His Lys Arg Leu Leu Lys
290                 295                 300 ttc ctg cac atc ttt ggc acc ctg ctg ccc cgg ccc tcc ttc ctc tac    960
Phe Leu His Ile Phe Gly Thr Leu Leu Pro Arg Pro Ser Phe Leu Tyr
305                 310                 315                 320 cgc acc atc caa gat ttg ggc atc ggc aca ttc cga gac ttg gcc gtg   1008
Arg Thr Ile Gln Asp Leu Gly Ile Gly Thr Phe Arg Asp Leu Ala Val
                325                 330                 335 gtg ctg gaa acg gcg ccc atc ctg acc gca ctg gac atc ttc gtg gac   1056
Val Leu Glu Thr Ala Pro Ile Leu Thr Ala Leu Asp Ile Phe Val Asp
        340                 345                 350 cgg cgt gtg tct gcg ctg cct gtg gtc aac gaa act gga cag gta gtg   1104
Arg Arg Val Ser Ala Leu Pro Val Val Asn Glu Thr Gly Gln Val Val
    355                 360                 365 ggc ctc tac tct cgc ttt gat gtg atc cac ctg gct gcc caa caa aca   1152
Gly Leu Tyr Ser Arg Phe Asp Val Ile His Leu Ala Ala Gln Gln Thr
370                 375                 380 tac aac cac ctg gac atg aat gtg gga gaa gcc ctg agg cag cgg aca   1200
Tyr Asn His Leu Asp Met Asn Val Gly Glu Ala Leu Arg Gln Arg Thr
385                 390                 395                 400 ctg tgt ctg gaa ggc gtc ctt tcc tgc cag ccc cac gag acc ttg ggg   1248
Leu Cys Leu Glu Gly Val Leu Ser Cys Gln Pro His Glu Thr Leu Gly
                405                 410                 415 gaa gtc att gac cgg att gtc cgg gaa cag gtg cac cgc ctg gtg ctc   1296
Glu Val Ile Asp Arg Ile Val Arg Glu Gln Val His Arg Leu Val Leu
        420                 425                 430
```

```
gtg gat gag acc cag cac ctt ctg ggc gtg gtg tcc ctc tct gac atc    1344
Val Asp Glu Thr Gln His Leu Leu Gly Val Val Ser Leu Ser Asp Ile
        435                 440                 445 ctt cag gct ctg gtg ctc agc cct gct gga att gat gcc ctc ggg gcc    1392
Leu Gln Ala Leu Val Leu Ser Pro Ala Gly Ile Asp Ala Leu Gly Ala
    450                 455                 460 tgagaacctt ggaacctttg ctctcaggcc acctggcaca cctggaagcc agtgaaggga   1452
gccgtggact cagctctcac ttcccctcag ccccacttgc tggtctggct cttgttcagg   1512
taggctccgc ccggggcccc tggcctcagc atcagcccct cagtctccct gggcacccag   1572
atctcagact ggggcaccct gaagatggga gtggcccagc ttatagctga gcagccttgt   1632
gaaatctacc agcatcaaga ctcactgtgg gaccactgct ttgtcccatt ctcagctgaa   1692
atgatggagg gcctcataag agggtggac agggcctgga gtagaggcca gatcagtgac    1752
gtgccttcag gacctccggg gagttagagc tgccctctct cagttcagtt ccccctgct    1812 gagaatgtcc ctggaaggaa gccagttaat aaaccttggt tggatggaat ttggagagtc   1872
g                                                                  1873
```

<210> SEQ ID NO 2
<211> LENGTH: 464
<212> TYPE: PRT
<213> ORGANISM: Sus scrofa

<400> SEQUENCE: 2

```
Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Asn Lys Ala
            20                  25                  30

Ser Arg Trp Thr Arg Gln Glu Asp Val Glu Glu Gly Gly Pro Pro Gly
        35                  40                  45

Pro Arg Glu Gly Pro Gln Ser Arg Pro Val Ala Glu Ser Thr Gly Gln
    50                  55                  60

Glu Ala Thr Phe Pro Lys Ala Thr Pro Leu Ala Gln Ala Ala Pro Leu
65                  70                  75                  80

Ala Glu Val Asp Asn Pro Pro Thr Glu Arg Asp Ile Leu Pro Ser Asp
                85                  90                  95

Cys Ala Ala Ser Ala Ser Asp Ser Asn Thr Asp His Leu Asp Leu Gly
            100                 105                 110

Ile Glu Phe Ser Ala Ser Ala Ala Ser Gly Asp Glu Leu Gly Leu Val
        115                 120                 125

Glu Glu Lys Pro Ala Pro Cys Pro Ser Pro Glu Val Leu Leu Pro Arg
    130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
                165                 170                 175

Lys Leu Val Ile Phe Asp Thr Met Leu Glu Ile Lys Lys Ala Phe Phe
            180                 185                 190

Ala Leu Val Ala Asn Gly Val Arg Ala Ala Pro Leu Trp Asp Ser Lys
        195                 200                 205

Lys Gln Ser Phe Val Gly Met Leu Thr Ile Thr Asp Phe Ile Leu Val
    210                 215                 220

Leu His Arg Tyr Tyr Arg Ser Pro Leu Val Gln Ile Tyr Glu Ile Glu
225                 230                 235                 240
```

```
Glu His Lys Ile Glu Thr Trp Arg Glu Ile Tyr Leu Gln Gly Cys Phe
                245                 250                 255

Lys Pro Leu Val Ser Ile Ser Pro Asn Asp Ser Leu Phe Glu Ala Val
            260                 265                 270

Tyr Ala Leu Ile Lys Asn Arg Ile His Arg Leu Pro Val Leu Asp Pro
        275                 280                 285

Val Ser Gly Ala Val Leu His Ile Leu Thr His Lys Arg Leu Leu Lys
    290                 295                 300

Phe Leu His Ile Phe Gly Thr Leu Leu Pro Arg Pro Ser Phe Leu Tyr
305                 310                 315                 320

Arg Thr Ile Gln Asp Leu Gly Ile Gly Thr Phe Arg Asp Leu Ala Val
                325                 330                 335

Val Leu Glu Thr Ala Pro Ile Leu Thr Ala Leu Asp Ile Phe Val Asp
            340                 345                 350

Arg Arg Val Ser Ala Leu Pro Val Val Asn Glu Thr Gly Gln Val Val
        355                 360                 365

Gly Leu Tyr Ser Arg Phe Asp Val Ile His Leu Ala Ala Gln Gln Thr
    370                 375                 380

Tyr Asn His Leu Asp Met Asn Val Gly Glu Ala Leu Arg Gln Arg Thr
385                 390                 395                 400

Leu Cys Leu Glu Gly Val Leu Ser Cys Gln Pro His Glu Thr Leu Gly
                405                 410                 415

Glu Val Ile Asp Arg Ile Val Arg Glu Gln Val His Arg Leu Val Leu
            420                 425                 430

Val Asp Glu Thr Gln His Leu Leu Gly Val Val Ser Leu Ser Asp Ile
        435                 440                 445

Leu Gln Ala Leu Val Leu Ser Pro Ala Gly Ile Asp Ala Leu Gly Ala
    450                 455                 460

<210> SEQ ID NO 3
<211> LENGTH: 1873
<212> TYPE: DNA
<213> ORGANISM: Sus scrofa
<220> FEATURE:
<221> NAME/KEY: CDS
<222> LOCATION: (1)..(1392)
<223> OTHER INFORMATION:

<400> SEQUENCE: 3 atg agc ttc cta gag caa gga gag agc cgt tca tgg cca tcc cga gct      48
Met Ser Phe Leu Glu Gln Gly Glu Ser Arg Ser Trp Pro Ser Arg Ala
1               5                   10                  15 gta acc acc agc tca gaa aga agc cat ggg gac cag ggg acc aag gcc      96
Val Thr Thr Ser Ser Glu Arg Ser His Gly Asp Gln Gly Thr Lys Ala
            20                  25                  30 tct aga tgg aca agg cag gag gat gta gag gaa ggg ggg cct ccg ggc     144
Ser Arg Trp Thr Arg Gln Glu Asp Val Glu Glu Gly Gly Pro Pro Gly
        35                  40                  45 ccg agg gaa ggt ccc cag tcc agg cca gtt gct gag tcc acc ggg cag     192
Pro Arg Glu Gly Pro Gln Ser Arg Pro Val Ala Glu Ser Thr Gly Gln
    50                  55                  60 gag gcc aca ttc ccc aag gcc aca ccc ttg gcc caa gcc gct ccc ttg     240
Glu Ala Thr Phe Pro Lys Ala Thr Pro Leu Ala Gln Ala Ala Pro Leu
65                  70                  75                  80 gcc gag gtg gac aac ccc cca aca gag cgg gac atc ctc ccc tct gac     288
Ala Glu Val Asp Asn Pro Pro Thr Glu Arg Asp Ile Leu Pro Ser Asp
                85                  90                  95
```

-continued

| | |
|---|---|
| tgt gca gcc tca gcc tcc gac tcc aac aca gac cat ctg gat ctg ggc<br>Cys Ala Ala Ser Ala Ser Asp Ser Asn Thr Asp His Leu Asp Leu Gly<br>              100                    105                    110 | 336 |
| ata gag ttc tca gcc tcg gcg gcg tcg ggg gat gag ctt ggg ctg gtg<br>Ile Glu Phe Ser Ala Ser Ala Ala Ser Gly Asp Glu Leu Gly Leu Val<br>              115                    120                    125 | 384 |
| gaa gag aag cca gcc ccg tgc cca tcc cca gag gtg ctg tta ccc agg<br>Glu Glu Lys Pro Ala Pro Cys Pro Ser Pro Glu Val Leu Leu Pro Arg<br>130                    135                    140 | 432 |
| ctg ggc tgg gat gat gag ctg cag aag ccg ggg gcc cag gtc tac atg<br>Leu Gly Trp Asp Asp Glu Leu Gln Lys Pro Gly Ala Gln Val Tyr Met<br>145                    150                    155                    160 | 480 |
| cac ttc atg cag gag cac acc tgc tac gat gcc atg gcg acc agc tcc<br>His Phe Met Gln Glu His Thr Cys Tyr Asp Ala Met Ala Thr Ser Ser<br>              165                    170                    175 | 528 |
| aaa ctg gtc atc ttc gac acc atg ctg gag atc aag aag gcc ttc ttt<br>Lys Leu Val Ile Phe Asp Thr Met Leu Glu Ile Lys Lys Ala Phe Phe<br>              180                    185                    190 | 576 |
| gcc ctg gtg gcc aac ggc gtc cga gcg gca cct ttg tgg gac agc aag<br>Ala Leu Val Ala Asn Gly Val Arg Ala Ala Pro Leu Trp Asp Ser Lys<br>              195                    200                    205 | 624 |
| aag cag agc ttc gtg ggg atg ctg acc atc aca gac ttc atc ttg gtg<br>Lys Gln Ser Phe Val Gly Met Leu Thr Ile Thr Asp Phe Ile Leu Val<br>            210                    215                    220 | 672 |
| ctg cac cgc tat tac agg tcc ccc ctg gtc cag atc tac gag att gaa<br>Leu His Arg Tyr Tyr Arg Ser Pro Leu Val Gln Ile Tyr Glu Ile Glu<br>225                    230                    235                    240 | 720 |
| gaa cat aag att gag acc tgg agg gag atc tac ctt caa ggc tgc ttc<br>Glu His Lys Ile Glu Thr Trp Arg Glu Ile Tyr Leu Gln Gly Cys Phe<br>                      245                    250                    255 | 768 |
| aag cct ctg gtc tcc atc tct ccc aat gac agc ctg ttc gaa gct gtc<br>Lys Pro Leu Val Ser Ile Ser Pro Asn Asp Ser Leu Phe Glu Ala Val<br>              260                    265                    270 | 816 |
| tac gcc ctc atc aag aac cgg atc cac cgc ctg ccg gtc ctg gac cct<br>Tyr Ala Leu Ile Lys Asn Arg Ile His Arg Leu Pro Val Leu Asp Pro<br>275                    280                    285 | 864 |
| gtc tcc ggg gct gtg ctc cac atc ctc aca cat aag cgg ctt ctc aag<br>Val Ser Gly Ala Val Leu His Ile Leu Thr His Lys Arg Leu Leu Lys<br>            290                    295                    300 | 912 |
| ttc ctg cac atc ttt ggc acc ctg ctg ccc cgg ccc tcc ttc ctc tac<br>Phe Leu His Ile Phe Gly Thr Leu Leu Pro Arg Pro Ser Phe Leu Tyr<br>305                    310                    315                    320 | 960 |
| cgc acc atc caa gat ttg ggc atc ggc aca ttc cga gac ttg gcc gtg<br>Arg Thr Ile Gln Asp Leu Gly Ile Gly Thr Phe Arg Asp Leu Ala Val<br>                    325                    330                    335 | 1008 |
| gtg ctg gaa acg gcg ccc atc ctg acc gca ctg gac atc ttc gtg gac<br>Val Leu Glu Thr Ala Pro Ile Leu Thr Ala Leu Asp Ile Phe Val Asp<br>            340                    345                    350 | 1056 |
| cgg cgt gtg tct gcg ctg cct gtg gtc aac gaa act gga cag gta gtg<br>Arg Arg Val Ser Ala Leu Pro Val Val Asn Glu Thr Gly Gln Val Val<br>              355                    360                    365 | 1104 |
| ggc ctc tac tct cgc ttt gat gtg atc cac ctg gct gcc caa caa aca<br>Gly Leu Tyr Ser Arg Phe Asp Val Ile His Leu Ala Ala Gln Gln Thr<br>370                    375                    380 | 1152 |
| tac aac cac ctg gac atg aat gtg gga gaa gcc ctg agg cag cgg aca<br>Tyr Asn His Leu Asp Met Asn Val Gly Glu Ala Leu Arg Gln Arg Thr<br>385                    390                    395                    400 | 1200 |
| ctg tgt ctg gaa ggc gtc ctt tcc tgc cag ccc cac gag acc ttg ggg<br>Leu Cys Leu Glu Gly Val Leu Ser Cys Gln Pro His Glu Thr Leu Gly | 1248 |

-continued

| | | |
|---|---|---|
| gaa gtc att gac cgg att gtc cgg gaa cag gtg cac cgc ctg gtg ctc<br>Glu Val Ile Asp Arg Ile Val Arg Glu Gln Val His Arg Leu Val Leu<br>            420                    425                  430 | | 1296 |
| gtg gat gag acc cag cac ctt ctg ggc gtg gtg tcc ctc tct gac atc<br>Val Asp Glu Thr Gln His Leu Leu Gly Val Val Ser Leu Ser Asp Ile<br>            435                    440                  445 | | 1344 |
| ctt cag gct ctg gtg ctc agc cct gct gga att gat gcc ctc ggg gcc<br>Leu Gln Ala Leu Val Leu Ser Pro Ala Gly Ile Asp Ala Leu Gly Ala<br>450                    455                  460 | | 1392 |
| tgagaacctt ggaacctttg ctctcaggcc acctggcaca cctggaagcc agtgaaggga | | 1452 |
| gccgtggact cagctctcac ttcccctcag ccccacttgc tggtctggct cttgttcagg | | 1512 |
| taggctccgc ccggggcccc tggcctcagc atcagcccct cagtctccct gggcacccag | | 1572 |
| atctcagact ggggcaccct gaagatggga gtggcccagc ttatagctga gcagccttgt | | 1632 |
| gaaatctacc agcatcaaga ctcactgtgg gaccactgct tgtcccatt ctcagctgaa | | 1692 |
| atgatggagg gcctcataag aggggtggac agggcctgga gtagaggcca gatcagtgac | | 1752 |
| gtgccttcag gacctccggg gagttagagc tgccctctct cagttcagtt ccccctgct | | 1812 |
| gagaatgtcc ctggaaggaa gccagttaat aaaccttggt tggatggaat ttggagagtc | | 1872 |
| g | | 1873 |

<210> SEQ ID NO 4
<211> LENGTH: 464
<212> TYPE: PRT
<213> ORGANISM: Sus scrofa

<400> SEQUENCE: 4

Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Thr Lys Ala
            20                  25                  30

Ser Arg Trp Thr Arg Gln Glu Asp Val Glu Glu Gly Gly Pro Pro Gly
        35                  40                  45

Pro Arg Glu Gly Pro Gln Ser Arg Pro Val Ala Glu Ser Thr Gly Gln
    50                  55                  60

Glu Ala Thr Phe Pro Lys Ala Thr Pro Leu Ala Gln Ala Ala Pro Leu
65                  70                  75                  80

Ala Glu Val Asp Asn Pro Pro Thr Glu Arg Asp Ile Leu Pro Ser Asp
                85                  90                  95

Cys Ala Ala Ser Ala Ser Asp Ser Asn Thr Asp His Leu Asp Leu Gly
            100                 105                 110

Ile Glu Phe Ser Ala Ser Ala Ala Ser Gly Asp Glu Leu Gly Leu Val
        115                 120                 125

Glu Glu Lys Pro Ala Pro Cys Pro Ser Pro Glu Val Leu Leu Pro Arg
    130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
                165                 170                 175

Lys Leu Val Ile Phe Asp Thr Met Leu Glu Ile Lys Lys Ala Phe Phe
            180                 185                 190

Ala Leu Val Ala Asn Gly Val Arg Ala Ala Pro Leu Trp Asp Ser Lys
        195                 200                 205

```
Lys Gln Ser Phe Val Gly Met Leu Thr Ile Thr Asp Phe Ile Leu Val
    210                 215                 220
Leu His Arg Tyr Tyr Arg Ser Pro Leu Val Gln Ile Tyr Glu Ile Glu
225                 230                 235                 240
Glu His Lys Ile Glu Thr Trp Arg Glu Ile Tyr Leu Gln Gly Cys Phe
                245                 250                 255
Lys Pro Leu Val Ser Ile Ser Pro Asn Asp Ser Leu Phe Glu Ala Val
            260                 265                 270
Tyr Ala Leu Ile Lys Asn Arg Ile His Arg Leu Pro Val Leu Asp Pro
        275                 280                 285
Val Ser Gly Ala Val Leu His Ile Leu Thr His Lys Arg Leu Leu Lys
    290                 295                 300
Phe Leu His Ile Phe Gly Thr Leu Leu Pro Arg Pro Ser Phe Leu Tyr
305                 310                 315                 320
Arg Thr Ile Gln Asp Leu Gly Ile Gly Thr Phe Arg Asp Leu Ala Val
                325                 330                 335
Val Leu Glu Thr Ala Pro Ile Leu Thr Ala Leu Asp Ile Phe Val Asp
            340                 345                 350
Arg Arg Val Ser Ala Leu Pro Val Val Asn Glu Thr Gly Gln Val Val
        355                 360                 365
Gly Leu Tyr Ser Arg Phe Asp Val Ile His Leu Ala Ala Gln Gln Thr
    370                 375                 380
Tyr Asn His Leu Asp Met Asn Val Gly Glu Ala Leu Arg Gln Arg Thr
385                 390                 395                 400
Leu Cys Leu Glu Gly Val Leu Ser Cys Gln Pro His Glu Thr Leu Gly
                405                 410                 415
Glu Val Ile Asp Arg Ile Val Arg Glu Gln Val His Arg Leu Val Leu
            420                 425                 430
Val Asp Glu Thr Gln His Leu Leu Gly Val Val Ser Leu Ser Asp Ile
        435                 440                 445
Leu Gln Ala Leu Val Leu Ser Pro Ala Gly Ile Asp Ala Leu Gly Ala
    450                 455                 460

<210> SEQ ID NO 5
<211> LENGTH: 1873
<212> TYPE: DNA
<213> ORGANISM: Sus scrofa
<220> FEATURE:
<221> NAME/KEY: CDS
<222> LOCATION: (1)..(1392)
<223> OTHER INFORMATION:

<400> SEQUENCE: 5 atg agc ttc cta gag caa gga gag agc cgt tca tgg cca tcc cga gct     48
Met Ser Phe Leu Glu Gln Gly Glu Ser Arg Ser Trp Pro Ser Arg Ala
1               5                   10                  15 gta acc acc agc tca gaa aga agc cat ggg gac cag ggg aac aag gcc     96
Val Thr Thr Ser Ser Glu Arg Ser His Gly Asp Gln Gly Asn Lys Ala
                20                  25                  30 tct aga tgg aca agg cag gag gat gta gag gaa ggg ggg cct ccg ggc    144
Ser Arg Trp Thr Arg Gln Glu Asp Val Glu Glu Gly Gly Pro Pro Gly
            35                  40                  45 ccg agg gaa agt ccc cag tcc agg cca gtt gct gag tcc acc ggg cag    192
Pro Arg Glu Ser Pro Gln Ser Arg Pro Val Ala Glu Ser Thr Gly Gln
        50                  55                  60 gag gcc aca ttc ccc aag gcc aca ccc ttg gcc caa gcc gct ccc ttg    240
Glu Ala Thr Phe Pro Lys Ala Thr Pro Leu Ala Gln Ala Ala Pro Leu
65                  70                  75                  80
```

-continued

| | |
|---|---|
| gcc gag gtg gac aac ccc cca aca gag cgg gac atc ctc ccc tct gac<br>Ala Glu Val Asp Asn Pro Pro Thr Glu Arg Asp Ile Leu Pro Ser Asp<br>                85                    90                95 | 288 |
| tgt gca gcc tca gcc tcc gac tcc aac aca gac cat ctg gat ctg ggc<br>Cys Ala Ala Ser Ala Ser Asp Ser Asn Thr Asp His Leu Asp Leu Gly<br>           100                   105              110 | 336 |
| ata gag ttc tca gcc tcg gcg gcg tcg ggg gat gag ctt ggg ctg gtg<br>Ile Glu Phe Ser Ala Ser Ala Ala Ser Gly Asp Glu Leu Gly Leu Val<br>        115                  120              125 | 384 |
| gaa gag aag cca gcc ccg tgc cca tcc cca gag gtg ctg tta ccc agg<br>Glu Glu Lys Pro Ala Pro Cys Pro Ser Pro Glu Val Leu Leu Pro Arg<br>130                   135               140 | 432 |
| ctg ggc tgg gat gat gag ctg cag aag ccg ggg gcc cag gtc tac atg<br>Leu Gly Trp Asp Asp Glu Leu Gln Lys Pro Gly Ala Gln Val Tyr Met<br>145                   150               155              160 | 480 |
| cac ttc atg cag gag cac acc tgc tac gat gcc atg gcg acc agc tcc<br>His Phe Met Gln Glu His Thr Cys Tyr Asp Ala Met Ala Thr Ser Ser<br>                165               170              175 | 528 |
| aaa ctg gtc atc ttc gac acc atg ctg gag atc aag aag gcc ttc ttt<br>Lys Leu Val Ile Phe Asp Thr Met Leu Glu Ile Lys Lys Ala Phe Phe<br>        180                  185              190 | 576 |
| gcc ctg gtg gcc aac ggc gtc cga gcg gca cct ttg tgg gac agc aag<br>Ala Leu Val Ala Asn Gly Val Arg Ala Ala Pro Leu Trp Asp Ser Lys<br>         195                 200              205 | 624 |
| aag cag agc ttc gtg ggg atg ctg acc atc aca gac ttc atc ttg gtg<br>Lys Gln Ser Phe Val Gly Met Leu Thr Ile Thr Asp Phe Ile Leu Val<br>210                   215              220 | 672 |
| ctg cac cgc tat tac agg tcc ccc ctg gtc cag atc tac gag att gaa<br>Leu His Arg Tyr Tyr Arg Ser Pro Leu Val Gln Ile Tyr Glu Ile Glu<br>225                   230               235              240 | 720 |
| gaa cat aag att gag acc tgg agg gag atc tac ctt caa ggc tgc ttc<br>Glu His Lys Ile Glu Thr Trp Arg Glu Ile Tyr Leu Gln Gly Cys Phe<br>                245               250              255 | 768 |
| aag cct ctg gtc tcc atc tct ccc aat gac agc ctg ttc gaa gct gtc<br>Lys Pro Leu Val Ser Ile Ser Pro Asn Asp Ser Leu Phe Glu Ala Val<br>        260                  265              270 | 816 |
| tac gcc ctc atc aag aac cgg atc cac cgc ctg ccg gtc ctg gac cct<br>Tyr Ala Leu Ile Lys Asn Arg Ile His Arg Leu Pro Val Leu Asp Pro<br>         275                 280              285 | 864 |
| gtc tcc ggg gct gtg ctc cac atc ctc aca cat aag cgg ctt ctc aag<br>Val Ser Gly Ala Val Leu His Ile Leu Thr His Lys Arg Leu Leu Lys<br>290                   295              300 | 912 |
| ttc ctg cac atc ttt ggc acc ctg ctg ccc cgg ccc tcc ttc ctc tac<br>Phe Leu His Ile Phe Gly Thr Leu Leu Pro Arg Pro Ser Phe Leu Tyr<br>305                   310               315              320 | 960 |
| cgc acc atc caa gat ttg ggc atc ggc aca ttc cga gac ttg gcc gtg<br>Arg Thr Ile Gln Asp Leu Gly Ile Gly Thr Phe Arg Asp Leu Ala Val<br>                325               330              335 | 1008 |
| gtg ctg gaa acg gcg ccc atc ctg acc gca ctg gac atc ttc gtg gac<br>Val Leu Glu Thr Ala Pro Ile Leu Thr Ala Leu Asp Ile Phe Val Asp<br>        340                 345              350 | 1056 |
| cgg cgt gtg tct gcg ctg cct gtg gtc aac gaa act gga cag gta gtg<br>Arg Arg Val Ser Ala Leu Pro Val Val Asn Glu Thr Gly Gln Val Val<br>        355                 360              365 | 1104 |
| ggc ctc tac tct cgc ttt gat gtg atc cac ctg gct gcc caa caa aca<br>Gly Leu Tyr Ser Arg Phe Asp Val Ile His Leu Ala Ala Gln Gln Thr<br>370                   375              380 | 1152 |
| tac aac cac ctg gac atg aat gtg gga gaa gcc ctg agg cag cgg aca<br>Tyr Asn His Leu Asp Met Asn Val Gly Glu Ala Leu Arg Gln Arg Thr | 1200 |

-continued

```
                385                 390                 395                 400
ctg tgt ctg gaa ggc gtc ctt tcc tgc cag ccc cac gag acc ttg ggg          1248
Leu Cys Leu Glu Gly Val Leu Ser Cys Gln Pro His Glu Thr Leu Gly
                    405                 410                 415 gaa gtc att gac cgg att gtc cgg gaa cag gtg cac cgc ctg gtg ctc          1296
Glu Val Ile Asp Arg Ile Val Arg Glu Gln Val His Arg Leu Val Leu
                420                 425                 430 gtg gat gag acc cag cac ctt ctg ggc gtg gtg tcc ctc tct gac atc          1344
Val Asp Glu Thr Gln His Leu Leu Gly Val Val Ser Leu Ser Asp Ile
            435                 440                 445 ctt cag gct ctg gtg ctc agc cct gct gga att gat gcc ctc ggg gcc          1392
Leu Gln Ala Leu Val Leu Ser Pro Ala Gly Ile Asp Ala Leu Gly Ala
        450                 455                 460 tgagaacctt ggaacctttg ctctcaggcc acctggcaca cctggaagcc agtgaaggga       1452
gccgtggact cagctctcac ttcccctcag ccccacttgc tggtctggct cttgttcagg       1512
taggctccgc ccggggcccc tggcctcagc atcagcccct cagtctccct gggcacccag       1572
atctcagact ggggcaccct gaagatggga gtggcccagc ttatagctga gcagccttgt       1632
gaaatctacc agcatcaaga ctcactgtgg gaccactgct ttgtcccatt ctcagctgaa       1692
atgatggagg gcctcataag aggggtggac agggcctgga gtagaggcca gatcagtgac       1752
gtgccttcag gacctccggg gagttagagc tgccctctct cagttcagtt ccccctgct       1812 gagaatgtcc ctggaaggaa gccagttaat aaaccttggt tggatggaat ttggagagtc       1872
g                                                                       1873

<210> SEQ ID NO 6
<211> LENGTH: 464
<212> TYPE: PRT
<213> ORGANISM: Sus scrofa

<400> SEQUENCE: 6

Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Asn Lys Ala
                20                  25                  30

Ser Arg Trp Thr Arg Gln Glu Asp Val Glu Glu Gly Gly Pro Pro Gly
            35                  40                  45

Pro Arg Glu Ser Pro Gln Ser Arg Pro Val Ala Glu Ser Thr Gly Gln
        50                  55                  60

Glu Ala Thr Phe Pro Lys Ala Thr Pro Leu Ala Gln Ala Ala Pro Leu
65                  70                  75                  80

Ala Glu Val Asp Asn Pro Pro Thr Glu Arg Asp Ile Leu Pro Ser Asp
                85                  90                  95

Cys Ala Ala Ser Ala Ser Asp Ser Asn Thr Asp His Leu Asp Leu Gly
            100                 105                 110

Ile Glu Phe Ser Ala Ser Ala Ala Ser Gly Asp Glu Leu Gly Leu Val
        115                 120                 125

Glu Glu Lys Pro Ala Pro Cys Pro Ser Pro Glu Val Leu Leu Pro Arg
    130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
                165                 170                 175

Lys Leu Val Ile Phe Asp Thr Met Leu Glu Ile Lys Lys Ala Phe Phe
            180                 185                 190
```

```
Ala Leu Val Ala Asn Gly Val Arg Ala Ala Pro Leu Trp Asp Ser Lys
        195                 200                 205

Lys Gln Ser Phe Val Gly Met Leu Thr Ile Thr Asp Phe Ile Leu Val
    210                 215                 220

Leu His Arg Tyr Tyr Arg Ser Pro Leu Val Gln Ile Tyr Glu Ile Glu
225                 230                 235                 240

Glu His Lys Ile Glu Thr Trp Arg Glu Ile Tyr Leu Gln Gly Cys Phe
                245                 250                 255

Lys Pro Leu Val Ser Ile Ser Pro Asn Asp Ser Leu Phe Glu Ala Val
            260                 265                 270

Tyr Ala Leu Ile Lys Asn Arg Ile His Arg Leu Pro Val Leu Asp Pro
        275                 280                 285

Val Ser Gly Ala Val Leu His Ile Leu Thr His Lys Arg Leu Leu Lys
    290                 295                 300

Phe Leu His Ile Phe Gly Thr Leu Leu Pro Arg Pro Ser Phe Leu Tyr
305                 310                 315                 320

Arg Thr Ile Gln Asp Leu Gly Ile Gly Thr Phe Arg Asp Leu Ala Val
                325                 330                 335

Val Leu Glu Thr Ala Pro Ile Leu Thr Ala Leu Asp Ile Phe Val Asp
            340                 345                 350

Arg Arg Val Ser Ala Leu Pro Val Val Asn Glu Thr Gly Gln Val Val
        355                 360                 365

Gly Leu Tyr Ser Arg Phe Asp Val Ile His Leu Ala Ala Gln Gln Thr
    370                 375                 380

Tyr Asn His Leu Asp Met Asn Val Gly Glu Ala Leu Arg Gln Arg Thr
385                 390                 395                 400

Leu Cys Leu Glu Gly Val Leu Ser Cys Gln Pro His Glu Thr Leu Gly
                405                 410                 415

Glu Val Ile Asp Arg Ile Val Arg Glu Gln Val His Arg Leu Val Leu
            420                 425                 430

Val Asp Glu Thr Gln His Leu Leu Gly Val Val Ser Leu Ser Asp Ile
        435                 440                 445

Leu Gln Ala Leu Val Leu Ser Pro Ala Gly Ile Asp Ala Leu Gly Ala
    450                 455                 460

<210> SEQ ID NO 7
<211> LENGTH: 1873
<212> TYPE: DNA
<213> ORGANISM: Sus scrofa
<220> FEATURE:
<221> NAME/KEY: CDS
<222> LOCATION: (1)..(1392)
<223> OTHER INFORMATION:

<400> SEQUENCE: 7 atg agc ttc cta gag caa gga gag agc cgt tca tgg cca tcc cga gct      48
Met Ser Phe Leu Glu Gln Gly Glu Ser Arg Ser Trp Pro Ser Arg Ala
1               5                   10                  15 gta acc acc agc tca gaa aga agc cat ggg gac cag ggg aac aag gcc      96
Val Thr Thr Ser Ser Glu Arg Ser His Gly Asp Gln Gly Asn Lys Ala
            20                  25                  30 tct aga tgg aca agg cag gag gat gta gag gaa ggg ggg cct ccg ggc     144
Ser Arg Trp Thr Arg Gln Glu Asp Val Glu Glu Gly Gly Pro Pro Gly
        35                  40                  45 ccg agg gaa ggt ccc cag tcc agg cca gtt gct gag tcc acc ggg cag     192
Pro Arg Glu Gly Pro Gln Ser Arg Pro Val Ala Glu Ser Thr Gly Gln
    50                  55                  60
```

-continued

| | |
|---|---|
| gag gcc aca ttc ccc aag gcc aca ccc ttg gcc caa gcc gct ccc ttg<br>Glu Ala Thr Phe Pro Lys Ala Thr Pro Leu Ala Gln Ala Ala Pro Leu<br>65                         70                     75                    80 | 240 |
| gcc gag gtg gac aac ccc cca aca gag cgg gac atc ctc ccc tct gac<br>Ala Glu Val Asp Asn Pro Pro Thr Glu Arg Asp Ile Leu Pro Ser Asp<br>                     85                     90                     95 | 288 |
| tgt gca gcc tca gcc tcc gac tcc aac aca gac cat ctg gat ctg ggc<br>Cys Ala Ala Ser Ala Ser Asp Ser Asn Thr Asp His Leu Asp Leu Gly<br>             100                   105                 110 | 336 |
| ata gag ttc tca gcc tcg gcg gcg tcg ggg gat gag ctt ggg ctg gtg<br>Ile Glu Phe Ser Ala Ser Ala Ala Ser Gly Asp Glu Leu Gly Leu Val<br>            115                   120                 125 | 384 |
| gaa gag aag cca gcc ccg tgc cca tcc cca gag gtg ctg tta ccc agg<br>Glu Glu Lys Pro Ala Pro Cys Pro Ser Pro Glu Val Leu Leu Pro Arg<br>130                        135                     140 | 432 |
| ctg ggc tgg gat gat gag ctg cag aag ccg ggg gcc cag gtc tac atg<br>Leu Gly Trp Asp Asp Glu Leu Gln Lys Pro Gly Ala Gln Val Tyr Met<br>145                        150                   155                 160 | 480 |
| cac ttc atg cag gag cac acc tgc tac gat gcc atg gcg acc agc tcc<br>His Phe Met Gln Glu His Thr Cys Tyr Asp Ala Met Ala Thr Ser Ser<br>            165                   170                 175 | 528 |
| aaa ctg gtc atc ttc gac acc atg ctg gag atc aag aag gcc ttc ttt<br>Lys Leu Val Ile Phe Asp Thr Met Leu Glu Ile Lys Lys Ala Phe Phe<br>            180                   185                 190 | 576 |
| gcc ctg gtg gcc aac ggc atc cga gcg gca cct ttg tgg gac agc aag<br>Ala Leu Val Ala Asn Gly Ile Arg Ala Ala Pro Leu Trp Asp Ser Lys<br>            195                   200                 205 | 624 |
| aag cag agc ttc gtg ggg atg ctg acc atc aca gac ttc atc ttg gtg<br>Lys Gln Ser Phe Val Gly Met Leu Thr Ile Thr Asp Phe Ile Leu Val<br>            210                   215                 220 | 672 |
| ctg cac cgc tat tac agg tcc ccc ctg gtc cag atc tac gag att gaa<br>Leu His Arg Tyr Tyr Arg Ser Pro Leu Val Gln Ile Tyr Glu Ile Glu<br>225                        230                   235                 240 | 720 |
| gaa cat aag att gag acc tgg agg gag atc tac ctt caa ggc tgc ttc<br>Glu His Lys Ile Glu Thr Trp Arg Glu Ile Tyr Leu Gln Gly Cys Phe<br>            245                   250                 255 | 768 |
| aag cct ctg gtc tcc atc tct ccc aat gac agc ctg ttc gaa gct gtc<br>Lys Pro Leu Val Ser Ile Ser Pro Asn Asp Ser Leu Phe Glu Ala Val<br>            260                   265                 270 | 816 |
| tac gcc ctc atc aag aac cgg atc cac cgc ctg ccg gtc ctg gac cct<br>Tyr Ala Leu Ile Lys Asn Arg Ile His Arg Leu Pro Val Leu Asp Pro<br>            275                   280                 285 | 864 |
| gtc tcc ggg gct gtg ctc cac atc ctc aca cat aag cgg ctt ctc aag<br>Val Ser Gly Ala Val Leu His Ile Leu Thr His Lys Arg Leu Leu Lys<br>            290                   295                 300 | 912 |
| ttc ctg cac atc ttt ggc acc ctg ctg ccc cgg ccc tcc ttc ctc tac<br>Phe Leu His Ile Phe Gly Thr Leu Leu Pro Arg Pro Ser Phe Leu Tyr<br>305                        310                   315                 320 | 960 |
| cgc acc atc caa gat ttg ggc atc ggc aca ttc cga gac ttg gcc gtg<br>Arg Thr Ile Gln Asp Leu Gly Ile Gly Thr Phe Arg Asp Leu Ala Val<br>            325                   330                 335 | 1008 |
| gtg ctg gaa acg gcg ccc atc ctg acc gca ctg gac atc ttc gtg gac<br>Val Leu Glu Thr Ala Pro Ile Leu Thr Ala Leu Asp Ile Phe Val Asp<br>            340                   345                 350 | 1056 |
| cgg cgt gtg tct gcg ctg cct gtg gtc aac gaa act gga cag gta gtg<br>Arg Arg Val Ser Ala Leu Pro Val Val Asn Glu Thr Gly Gln Val Val<br>            355                   360                 365 | 1104 |
| ggc ctc tac tct cgc ttt gat gtg atc cac ctg gct gcc caa caa aca<br>Gly Leu Tyr Ser Arg Phe Asp Val Ile His Leu Ala Ala Gln Gln Thr | 1152 |

-continued

```
                370                 375                 380
tac aac cac ctg gac atg aat gtg gga gaa gcc ctg agg cag cgg aca    1200
Tyr Asn His Leu Asp Met Asn Val Gly Glu Ala Leu Arg Gln Arg Thr
385                 390                 395                 400 ctg tgt ctg gaa ggc gtc ctt tcc tgc cag ccc cac gag acc ttg ggg    1248
Leu Cys Leu Glu Gly Val Leu Ser Cys Gln Pro His Glu Thr Leu Gly
                405                 410                 415 gaa gtc att gac cgg att gtc cgg gaa cag gtg cac cgc ctg gtg ctc    1296
Glu Val Ile Asp Arg Ile Val Arg Glu Gln Val His Arg Leu Val Leu
            420                 425                 430 gtg gat gag acc cag cac ctt ctg ggc gtg gtg tcc ctc tct gac atc    1344
Val Asp Glu Thr Gln His Leu Leu Gly Val Val Ser Leu Ser Asp Ile
        435                 440                 445 ctt cag gct ctg gtg ctc agc cct gct gga att gat gcc ctc ggg gcc    1392
Leu Gln Ala Leu Val Leu Ser Pro Ala Gly Ile Asp Ala Leu Gly Ala
    450                 455                 460 tgagaaccctt ggaacctttg ctctcaggcc acctggcaca cctggaagcc agtgaaggga   1452
gccgtggact cagctctcac ttcccctcag ccccacttgc tggtctggct cttgttcagg    1512
taggctccgc ccggggcccc tggcctcagc atcagcccct cagtctccct gggcacccag    1572
atctcagact ggggcaccct gaagatggga gtggcccagc ttatagctga gcagccttgt    1632
gaaatctacc agcatcaaga ctcactgtgg gaccactgct ttgtcccatt ctcagctgaa    1692
atgatggagg gcctcataag aggggtggac agggcctgga gtagaggcca gatcagtgac    1752
gtgccttcag gacctccggg gagttagagc tgccctctct cagttcagtt ccccctgct    1812 gagaatgtcc ctggaaggaa gccagttaat aaaccttggt tggatggaat ttggagagtc   1872
g                                                                    1873
```

<210> SEQ ID NO 8
<211> LENGTH: 464
<212> TYPE: PRT
<213> ORGANISM: Sus scrofa

<400> SEQUENCE: 8

```
Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Asn Lys Ala
            20                  25                  30

Ser Arg Trp Thr Arg Gln Glu Asp Val Glu Glu Gly Gly Pro Pro Gly
        35                  40                  45

Pro Arg Glu Gly Pro Gln Ser Arg Pro Val Ala Glu Ser Thr Gly Gln
    50                  55                  60

Glu Ala Thr Phe Pro Lys Ala Thr Pro Leu Ala Gln Ala Ala Pro Leu
65                  70                  75                  80

Ala Glu Val Asp Asn Pro Pro Thr Glu Arg Asp Ile Leu Pro Ser Asp
                85                  90                  95

Cys Ala Ala Ser Ala Ser Asp Ser Asn Thr Asp His Leu Asp Leu Gly
            100                 105                 110

Ile Glu Phe Ser Ala Ser Ala Ala Ser Gly Asp Glu Leu Gly Leu Val
        115                 120                 125

Glu Glu Lys Pro Ala Pro Cys Pro Ser Pro Glu Val Leu Leu Pro Arg
    130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
```

```
                    165                 170                 175
Lys Leu Val Ile Phe Asp Thr Met Leu Glu Ile Lys Lys Ala Phe Phe
                180                 185                 190
Ala Leu Val Ala Asn Gly Ile Arg Ala Ala Pro Leu Trp Asp Ser Lys
                195                 200                 205
Lys Gln Ser Phe Val Gly Met Leu Thr Ile Thr Asp Phe Ile Leu Val
            210                 215                 220
Leu His Arg Tyr Tyr Arg Ser Pro Leu Val Gln Ile Tyr Glu Ile Glu
225                 230                 235                 240
Glu His Lys Ile Glu Thr Trp Arg Glu Ile Tyr Leu Gln Gly Cys Phe
                245                 250                 255
Lys Pro Leu Val Ser Ile Ser Pro Asn Asp Ser Leu Phe Glu Ala Val
            260                 265                 270
Tyr Ala Leu Ile Lys Asn Arg Ile His Arg Leu Pro Val Leu Asp Pro
        275                 280                 285
Val Ser Gly Ala Val Leu His Ile Leu Thr His Lys Arg Leu Leu Lys
    290                 295                 300
Phe Leu His Ile Phe Gly Thr Leu Leu Pro Arg Pro Ser Phe Leu Tyr
305                 310                 315                 320
Arg Thr Ile Gln Asp Leu Gly Ile Gly Thr Phe Arg Asp Leu Ala Val
                325                 330                 335
Val Leu Glu Thr Ala Pro Ile Leu Thr Ala Leu Asp Ile Phe Val Asp
                340                 345                 350
Arg Arg Val Ser Ala Leu Pro Val Val Asn Glu Thr Gly Gln Val Val
            355                 360                 365
Gly Leu Tyr Ser Arg Phe Asp Val Ile His Leu Ala Ala Gln Gln Thr
        370                 375                 380
Tyr Asn His Leu Asp Met Asn Val Gly Glu Ala Leu Arg Gln Arg Thr
385                 390                 395                 400
Leu Cys Leu Glu Gly Val Leu Ser Cys Gln Pro His Glu Thr Leu Gly
                405                 410                 415
Glu Val Ile Asp Arg Ile Val Arg Glu Gln Val His Arg Leu Val Leu
                420                 425                 430
Val Asp Glu Thr Gln His Leu Leu Gly Val Val Ser Leu Ser Asp Ile
            435                 440                 445
Leu Gln Ala Leu Val Leu Ser Pro Ala Gly Ile Asp Ala Leu Gly Ala
        450                 455                 460

<210> SEQ ID NO 9
<211> LENGTH: 1873
<212> TYPE: DNA
<213> ORGANISM: Sus scrofa
<220> FEATURE:
<221> NAME/KEY: CDS
<222> LOCATION: (1)..(1392)
<223> OTHER INFORMATION:

<400> SEQUENCE: 9 atg agc ttc cta gag caa gga gag agc cgt tca tgg cca tcc cga gct      48
Met Ser Phe Leu Glu Gln Gly Glu Ser Arg Ser Trp Pro Ser Arg Ala
1               5                   10                  15 gta acc acc agc tca gaa aga agc cat ggg gac cag ggg aac aag gcc      96
Val Thr Thr Ser Ser Glu Arg Ser His Gly Asp Gln Gly Asn Lys Ala
                20                  25                  30 tct aga tgg aca agg cag gag gat gta gag gaa ggg ggg cct ccg ggc     144
Ser Arg Trp Thr Arg Gln Glu Asp Val Glu Glu Gly Gly Pro Pro Gly
            35                  40                  45
```

-continued

```
ccg agg gaa ggt ccc cag tcc agg cca gtt gct gag tcc acc ggg cag    192
Pro Arg Glu Gly Pro Gln Ser Arg Pro Val Ala Glu Ser Thr Gly Gln
    50                  55                  60 gag gcc aca ttc ccc aag gcc aca ccc ttg gcc caa gcc gct ccc ttg    240
Glu Ala Thr Phe Pro Lys Ala Thr Pro Leu Ala Gln Ala Ala Pro Leu
65                  70                  75                  80 gcc gag gtg gac aac ccc cca aca gag cgg gac atc ctc ccc tct gac    288
Ala Glu Val Asp Asn Pro Pro Thr Glu Arg Asp Ile Leu Pro Ser Asp
                85                  90                  95 tgt gca gcc tca gcc tcc gac tcc aac aca gac cat ctg gat ctg ggc    336
Cys Ala Ala Ser Ala Ser Asp Ser Asn Thr Asp His Leu Asp Leu Gly
            100                 105                 110 ata gag ttc tca gcc tcg gcg gcg tcg ggg gat gag ctt ggg ctg gtg    384
Ile Glu Phe Ser Ala Ser Ala Ala Ser Gly Asp Glu Leu Gly Leu Val
        115                 120                 125 gaa gag aag cca gcc ccg tgc cca tcc cca gag gtg ctg tta ccc agg    432
Glu Glu Lys Pro Ala Pro Cys Pro Ser Pro Glu Val Leu Leu Pro Arg
    130                 135                 140 ctg ggc tgg gat gat gag ctg cag aag ccg ggg gcc cag gtc tac atg    480
Leu Gly Trp Asp Asp Glu Leu Gln Lys Pro Gly Ala Gln Val Tyr Met
145                 150                 155                 160 cac ttc atg cag gag cac acc tgc tac gat gcc atg gcg acc agc tcc    528
His Phe Met Gln Glu His Thr Cys Tyr Asp Ala Met Ala Thr Ser Ser
                165                 170                 175 aaa ctg gtc atc ttc gac acc atg ctg gag atc aag aag gcc ttc ttt    576
Lys Leu Val Ile Phe Asp Thr Met Leu Glu Ile Lys Lys Ala Phe Phe
            180                 185                 190 gcc ctg gtg gcc aac ggc gtc caa gcg gca cct ttg tgg gac agc aag    624
Ala Leu Val Ala Asn Gly Val Gln Ala Ala Pro Leu Trp Asp Ser Lys
        195                 200                 205 aag cag agc ttc gtg ggg atg ctg acc atc aca gac ttc atc ttg gtg    672
Lys Gln Ser Phe Val Gly Met Leu Thr Ile Thr Asp Phe Ile Leu Val
    210                 215                 220 ctg cac cgc tat tac agg tcc ccc ctg gtc cag atc tac gag att gaa    720
Leu His Arg Tyr Tyr Arg Ser Pro Leu Val Gln Ile Tyr Glu Ile Glu
225                 230                 235                 240 gaa cat aag att gag acc tgg agg gag atc tac ctt caa ggc tgc ttc    768
Glu His Lys Ile Glu Thr Trp Arg Glu Ile Tyr Leu Gln Gly Cys Phe
                245                 250                 255 aag cct ctg gtc tcc atc tct ccc aat gac agc ctg ttc gaa gct gtc    816
Lys Pro Leu Val Ser Ile Ser Pro Asn Asp Ser Leu Phe Glu Ala Val
            260                 265                 270 tac gcc ctc atc aag aac cgg atc cac cgc ctg ccg gtc ctg gac cct    864
Tyr Ala Leu Ile Lys Asn Arg Ile His Arg Leu Pro Val Leu Asp Pro
        275                 280                 285 gtc tcc ggg gct gtg ctc cac atc ctc aca cat aag cgg ctt ctc aag    912
Val Ser Gly Ala Val Leu His Ile Leu Thr His Lys Arg Leu Leu Lys
    290                 295                 300 ttc ctg cac atc ttt ggc acc ctg ctg ccc cgg ccc tcc ttc ctc tac    960
Phe Leu His Ile Phe Gly Thr Leu Leu Pro Arg Pro Ser Phe Leu Tyr
305                 310                 315                 320 cgc acc atc caa gat ttg ggc atc ggc aca ttc cga gac ttg gcc gtg    1008
Arg Thr Ile Gln Asp Leu Gly Ile Gly Thr Phe Arg Asp Leu Ala Val
                325                 330                 335 gtg ctg gaa acg gcg ccc atc ctg acc gca ctg gac atc ttc gtg gac    1056
Val Leu Glu Thr Ala Pro Ile Leu Thr Ala Leu Asp Ile Phe Val Asp
            340                 345                 350 cgg cgt gtg tct gcg ctg cct gtg gtc aac gaa act gga cag gta gtg    1104
Arg Arg Val Ser Ala Leu Pro Val Val Asn Glu Thr Gly Gln Val Val
```

|  |  |  |  |  |  |  |  |  |  |  |  |  |  |  |  |
|---|---|---|---|---|---|---|---|---|---|---|---|---|---|---|---|
| | | | 355 | | | | 360 | | | | | 365 | | | |
| ggc | ctc | tac | tct | cgc | ttt | gat | gtg | atc | cac | ctg | gct | gcc | caa | caa | aca | 1152 |
| Gly | Leu | Tyr | Ser | Arg | Phe | Asp | Val | Ile | His | Leu | Ala | Ala | Gln | Gln | Thr | |
| | 370 | | | | | 375 | | | | | 380 | | | | | |
| tac | aac | cac | ctg | gac | atg | aat | gtg | gga | gaa | gcc | ctg | agg | cag | cgg | aca | 1200 |
| Tyr | Asn | His | Leu | Asp | Met | Asn | Val | Gly | Glu | Ala | Leu | Arg | Gln | Arg | Thr | |
| 385 | | | | | 390 | | | | | 395 | | | | | 400 | |
| ctg | tgt | ctg | gaa | ggc | gtc | ctt | tcc | tgc | cag | ccc | cac | gag | acc | ttg | ggg | 1248 |
| Leu | Cys | Leu | Glu | Gly | Val | Leu | Ser | Cys | Gln | Pro | His | Glu | Thr | Leu | Gly | |
| | | | | 405 | | | | | 410 | | | | | 415 | | |
| gaa | gtc | att | gac | cgg | att | gtc | cgg | gaa | cag | gtg | cac | cgc | ctg | gtg | ctc | 1296 |
| Glu | Val | Ile | Asp | Arg | Ile | Val | Arg | Glu | Gln | Val | His | Arg | Leu | Val | Leu | |
| | | | 420 | | | | | 425 | | | | | 430 | | | |
| gtg | gat | gag | acc | cag | cac | ctt | ctg | ggc | gtg | gtg | tcc | ctc | tct | gac | atc | 1344 |
| Val | Asp | Glu | Thr | Gln | His | Leu | Leu | Gly | Val | Val | Ser | Leu | Ser | Asp | Ile | |
| | | 435 | | | | | 440 | | | | | 445 | | | | |
| ctt | cag | gct | ctg | gtg | ctc | agc | cct | gct | gga | att | gat | gcc | ctc | ggg | gcc | 1392 |
| Leu | Gln | Ala | Leu | Val | Leu | Ser | Pro | Ala | Gly | Ile | Asp | Ala | Leu | Gly | Ala | |
| | 450 | | | | | 455 | | | | | 460 | | | | | |

| | |
|---|---|
| tgagaaccctt ggaaccctttg ctctcaggcc acctggcaca cctggaagcc agtgaaggga | 1452 |
| gccgtggact cagctctcac ttcccctcag ccccacttgc tggtctggct cttgttcagg | 1512 |
| taggctccgc ccggggcccc tggcctcagc atcagcccct cagtctccct gggcacccag | 1572 |
| atctcagact ggggcaccct gaagatggga gtggcccagc ttatagctga gcagccttgt | 1632 |
| gaaatctacc agcatcaaga ctcactgtgg gaccactgct ttgtcccatt ctcagctgaa | 1692 |
| atgatggagg gcctcataag aggggtggac agggcctgga gtagaggcca gatcagtgac | 1752 |
| gtgccttcag gacctccggg gagttagagc tgccctctct cagttcagtt ccccccctgct | 1812 |
| gagaatgtcc ctggaaggaa gccagttaat aaaccttggt tggatggaat ttggagagtc | 1872 |
| g | 1873 |

<210> SEQ ID NO 10
<211> LENGTH: 464
<212> TYPE: PRT
<213> ORGANISM: Sus scrofa

<400> SEQUENCE: 10

Met Ser Phe Leu Glu Gln Gly Glu Ser Arg Ser Trp Pro Ser Arg Ala
1               5                   10                  15

Val Thr Thr Ser Ser Glu Arg Ser His Gly Asp Gln Gly Asn Lys Ala
            20                  25                  30

Ser Arg Trp Thr Arg Gln Glu Asp Val Glu Glu Gly Gly Pro Pro Gly
        35                  40                  45

Pro Arg Glu Gly Pro Gln Ser Arg Pro Val Ala Glu Ser Thr Gly Gln
    50                  55                  60

Glu Ala Thr Phe Pro Lys Ala Thr Pro Leu Ala Gln Ala Pro Leu
65                  70                  75                  80

Ala Glu Val Asp Asn Pro Pro Thr Glu Arg Asp Ile Leu Pro Ser Asp
                85                  90                  95

Cys Ala Ala Ser Ala Ser Asp Ser Asn Thr Asp His Leu Asp Leu Gly
            100                 105                 110

Ile Glu Phe Ser Ala Ser Ala Ser Gly Asp Glu Leu Gly Leu Val
        115                 120                 125

Glu Glu Lys Pro Ala Pro Cys Pro Ser Pro Glu Val Leu Leu Pro Arg
    130                 135                 140

Leu Gly Trp Asp Asp Glu Leu Gln Lys Pro Gly Ala Gln Val Tyr Met
145                 150                 155                 160

His Phe Met Gln Glu His Thr Cys Tyr Asp Ala Met Ala Thr Ser Ser
            165                 170                 175

Lys Leu Val Ile Phe Asp Thr Met Leu Glu Ile Lys Lys Ala Phe Phe
        180                 185                 190

Ala Leu Val Ala Asn Gly Val Gln Ala Ala Pro Leu Trp Asp Ser Lys
    195                 200                 205

Lys Gln Ser Phe Val Gly Met Leu Thr Ile Thr Asp Phe Ile Leu Val
210                 215                 220

Leu His Arg Tyr Tyr Arg Ser Pro Leu Val Gln Ile Tyr Glu Ile Glu
225                 230                 235                 240

Glu His Lys Ile Glu Thr Trp Arg Glu Ile Tyr Leu Gln Gly Cys Phe
                245                 250                 255

Lys Pro Leu Val Ser Ile Ser Pro Asn Asp Ser Leu Phe Glu Ala Val
            260                 265                 270

Tyr Ala Leu Ile Lys Asn Arg Ile His Arg Leu Pro Val Leu Asp Pro
        275                 280                 285

Val Ser Gly Ala Val Leu His Ile Leu Thr His Lys Arg Leu Leu Lys
    290                 295                 300

Phe Leu His Ile Phe Gly Thr Leu Leu Pro Arg Pro Ser Phe Leu Tyr
305                 310                 315                 320

Arg Thr Ile Gln Asp Leu Gly Ile Gly Thr Phe Arg Asp Leu Ala Val
                325                 330                 335

Val Leu Glu Thr Ala Pro Ile Leu Thr Ala Leu Asp Ile Phe Val Asp
            340                 345                 350

Arg Arg Val Ser Ala Leu Pro Val Val Asn Glu Thr Gly Gln Val Val
        355                 360                 365

Gly Leu Tyr Ser Arg Phe Asp Val Ile His Leu Ala Ala Gln Gln Thr
    370                 375                 380

Tyr Asn His Leu Asp Met Asn Val Gly Glu Ala Leu Arg Gln Arg Thr
385                 390                 395                 400

Leu Cys Leu Glu Gly Val Leu Ser Cys Gln Pro His Glu Thr Leu Gly
                405                 410                 415

Glu Val Ile Asp Arg Ile Val Arg Glu Gln Val His Arg Leu Val Leu
            420                 425                 430

Val Asp Glu Thr Gln His Leu Leu Gly Val Val Ser Leu Ser Asp Ile
        435                 440                 445

Leu Gln Ala Leu Val Leu Ser Pro Ala Gly Ile Asp Ala Leu Gly Ala
    450                 455                 460

<210> SEQ ID NO 11
<211> LENGTH: 1095
<212> TYPE: DNA
<213> ORGANISM: Sus scrofa

<400> SEQUENCE: 11
gaaactcttc tccccacaga ctccctcctg gagcagcctc ggggacccta agcatcaagg      60 taggtgggc tgcccctgct cgcgggccca ggctcttctc ccacctcctt ttcttccacg      120
tcttcaggac cccaatctcc cccactccac tcgcctggct cttgtcttcc ctcctttgc      180 cttctttgtt ccgctttgtt tcttcttcct ccctctccct cacctcctcc ctctttcaaa     240
agagtagagg gggcatctat agagtctgga gattgggact ctcttgactt tctcgcttac     300
tagctgtgtg atttgtggca aattgcttca cctctctgag ctcaggtctc tcgttagtaa     360

```
aacagggctg atagccatgc ccttcggata agattgccgt gagggttgaa tgagaaattt      420
gttggaggac aagccctttg aagcttccca atattaaata tttttattta tttatttatt      480
ttttgtcttt ttgctattcc tttgggccgc tcccacggca tatggaggtt cccaggctag      540
gggtcgaatc ggagctgtag ccactggcct acgccagagc cacagcaacg cgggatccga      600
gccgcatctg caacctacac cacagctcac ggcaacgccg gatcgttaac ccactgagca      660
ggggcaggca ccgaacctgc aacctcatgg ttcctagtgg gattcgttaa ccactgcgcc      720
acgacgggaa ctccccaata ttaaatatta ttattagtaa cattttaatg gaatttattg      780
tgttactccc cattaaccaa acaggtccca ttctcccttg cagagatgag cttcctagag      840
caaggagaga gccgttcatg gccatcccga gctgtgacca ccagctcaga agaagccat       900 ggggaccagg ggaccaaggc tctagatgg acaaggcagg aggatrtaga ggaaggggg        960 cctccgggcc cgagggaarg tgagttcaag gccagttctg gggagctggg actgggggca     1020
gtgggcagtc ctcaaacctg ggcccgtct ctggtctggt ccctccataa cacaggcaca      1080
taacatcatg cagcc                                                     1095
```

<210> SEQ ID NO 12
<211> LENGTH: 808
<212> TYPE: DNA
<213> ORGANISM: Sus scrofa

<400> SEQUENCE: 12

```
gaaactcttc tccccacaga ctccctcctg gagcagcctc ggggaccta agcatcaagg        60 taggtggggc tgcccctgct cgcgggccca ggctcttctc ccacctcctt ttcttccacg      120
tcttcaggac cccaatctcc cccactccac tcgcctggct cttgtcttcc tctcctttgc      180
cttctttgtt ccgctttgtt tcttcttcct ccctctccct cacctcctcc ctctttcaaa      240
agagtagagg gggcatctat agagtctgga gattgggact ctcttgactt tctcgcttac      300
tagctgtgtg atttgtggca aattgcttca cctctctgag ctcaggtctc tcgttagtaa      360
aacagggctg atagccatgc ccttcggata agattgccgt gagggttgaa tgagaaattt      420
gttggaggac aagccctttg aagcttccca atattaaata ttattattag taacatttta      480
atggaattta ttgtgttact ccccattaac caaacaggtc ccattctccc ttgcagagat      540
gagcttccta gagcaaggag agagccgttc atggccatcc cgagctgtga ccaccagctc      600
agaaagaagc catggggacc aggggaccaa ggcctctaga tggacaaggc aggaggatat      660
agaggaaggg gggcctccgg gcccgaggga argtgagttc aaggccagtt ctggggagct      720
gggactgggg gcagtgggca gtcctcaaac ctggggcccg tctctggtct ggtccctcca      780
taacacaggc acataacatc atgcagcc                                        808
```

<210> SEQ ID NO 13
<211> LENGTH: 21
<212> TYPE: DNA
<213> ORGANISM: Sus scrofa

<400> SEQUENCE: 13

```
atgagcttcc tagagcaagg a                                                21
```

<210> SEQ ID NO 14
<211> LENGTH: 22
<212> TYPE: DNA
<213> ORGANISM: Sus scrofa

```
<400> SEQUENCE: 14
ggctgcatga tgttatgtgc ct                                      22

<210> SEQ ID NO 15
<211> LENGTH: 21
<212> TYPE: DNA
<213> ORGANISM: Sus scrofa

<400> SEQUENCE: 15
gaaactcttc tccccacaga c                                       21

<210> SEQ ID NO 16
<211> LENGTH: 20
<212> TYPE: DNA
<213> ORGANISM: Sus scrofa

<400> SEQUENCE: 16
ggagcaaatg tgcagacaag                                         20

<210> SEQ ID NO 17
<211> LENGTH: 20
<212> TYPE: DNA
<213> ORGANISM: Sus scrofa

<400> SEQUENCE: 17
cccacgaagc tctgcttctt                                         20

<210> SEQ ID NO 18
<211> LENGTH: 23
<212> TYPE: DNA
<213> ORGANISM: Sus scrofa

<400> SEQUENCE: 18
caggtctcaa tcttatgttc ttc                                     23

<210> SEQ ID NO 19
<211> LENGTH: 20
<212> TYPE: DNA
<213> ORGANISM: Sus scrofa

<400> SEQUENCE: 19
cgtccgagcg gcacctttgc                                         20

<210> SEQ ID NO 20
<211> LENGTH: 21
<212> TYPE: DNA
<213> ORGANISM: Sus scrofa

<400> SEQUENCE: 20
aaggttccaa ggttctcagg c                                       21

<210> SEQ ID NO 21
<211> LENGTH: 21
<212> TYPE: DNA
<213> ORGANISM: Sus scrofa

<400> SEQUENCE: 21
tccttgctct aggaagctca t                                       21
```

PRKAG3 ALLELES AND USE OF THE SAME AS GENETIC MARKERS FOR REPRODUCTIVE AND MEAT QUALITY TRAITS

CROSS REFERENCE TO RELATED APPLICATION

This application is a continuation of the following co-pending commonly owned U.S. provisional applications: 60/231,045 filed Sep. 8, 2000; 60/260,239 filed Jan. 8, 2001; and 60/299,111 filed Jun. 18, 2001. Priority is claimed under 35 U.S.C. Section 120.

GRANT REFERENCE CLAUSE

This invention was supported at least in part by Project Number IOWO 3600 (Hatch Funds, USDA). The United States government may have certain rights in this invention.

FIELD OF THE INVENTION

This invention relates generally to the detection of genetic differences among animals. More particularly, the invention relates to genetic markers that are indicative of heritable phenotypes associated with improved meat quality, litter size and other economic traits in animals. Methods and compositions for use of these markers in genotyping of animals and selection are also disclosed.

BACKGROUND OF THE INVENTION

Genetic differences exist among individual animals as well as among breeds which can be exploited by breeding techniques to achieve animals with desirable characteristics. For example, Chinese breeds are known for reaching puberty at an early age and for their large litter size, while American breeds are known for their greater growth rates and leanness. Often, however, heritability for desired traits is low, and standard breeding methods which select individuals based upon phenotypic variations do not take fully into account genetic variability or complex gene interactions which exist.

Restriction fragment length polymorphism (RFLP) analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science,* Mar. 26–28, 1990, incorporated herein by reference, reports on the polymorphism of swine major histocompatibility complex (MHC) genes for Chinese pigs, also demonstrated by RFLP analysis. Jung et al., *Theor. Appl. Genet.,* 77:271–274 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency.

Litter size, of course has a direct economic impact for a breeder, also important for meat producing animals is meat quality. Meat quality is a difficult characteristic to assess, as many different aspects, both objective and subjective, make up the overall trait. The list of factors which determine quality in meat, as with other foods, is rather long (Wood et al., *Proceedings of The Nutrition Society* (1999) 58:363–70). It includes freedom from microbiological hazards (food safety) and prevention of animal exploitation (animal welfare). It also includes the sensory appeal of meat, i.e. its taste or eating quality, and perceived healthiness, especially in relation to the amount and type of fat.

The quality of raw pig meat is influenced by a large number of genetic and non-genetic factors. The latter include farm, transport, slaughter and processing conditions. Meat scientists have performed a substantial amount of research on these factors, which has led to considerable quality improvement. Part of the research has also been dedicated to the genetic background of the animals, and several studies have revealed the importance of genetic factors. This has made the industry aware that selective breeding of animals and the use of gene technology can play an important role in enhancing pork quality.

Information at DNA level can help to fix a specific major gene, but it can also assist the selection of quantitative trait for which we already select. Molecular information in addition to phenotypic data can increase the accuracy of selection and therefore the selection response. The size of the extra response in such a Marker Assisted Selection (MAS) program has been considered by many workers from a theoretical point of view. In general terms, MAS is more beneficial for traits with a low heritability and which are expensive to measure phenotypically. Meat quality in particular qualifies as an excellent opportunity to utilize MAS. For example, Meuwissen, T. H. E. and Goddard, M. E.(1996) "The use of Marker Haplotypes in Animal Breeding Schemes", Genet. Sel. Evol., 28 161–176 considered the impact of Marker Assisted Selection for traits such as reproduction and meat quality that are difficult to progress using traditional methods. their results are extremely encouraging, showing that for traits such as meat quality, where the trait is measured after slaughter, an additional response of up to 64% could be achieved.

Indeed, the best approach to genetically improve economic traits such as meat quality or litter size is to find relevant DNA-markers directly in the population under selection. Meat quality measurements can be performed continuously on some animals from the nucleus populations of breeding organizations. Since a full assessment of meat quality can only be done after slaughter, the data must be collected on culled animals and cannot be obtained on potential breeding animals. Similarly for litter size, females can be identified only after they have given birth to ascertain the size of litter. Identifying a genetic predisposition for these traits would allow selection at the genetic level.

This phenotypic data is collected in order to enable the detection of relevant DNA markers, and to validate markers identified using experimental populations or to test candidate genes. Significant markers or genes can then be included directly in the selection process. An advantage of the molecular information is that we can obtain it already at very young age of the breeding animal, which means that animals can be preselected based on DNA markers before the growing performance test is completed. This is a great advantage for the overall testing and selection system.

It can be seen from the foregoing that a need exists for identification of markers which may be used to improve meat quality as well as reproduction characteristics in animals by identifying and selecting animals with the improved characteristics at the genetic level.

An object of the present invention is to provide a genetic marker based on or within the PRKAG3 gene which is indicative of favorable meat characteristics such as those evidenced by pH, marbling, color and drip loss and or for larger litter size.

Another object of the invention is to provide an assay for determining the presence of this genetic marker.

A further object of the invention is to provide a method of evaluating animals that increases accuracy of selection and breeding methods for the desired traits.

Yet another object of the invention is to provide a PCR amplification test which will greatly expedite the determination of presence of the marker.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

This invention relates to the discovery of alternate gene forms of the PRKAG3 gene which are useful as genetic markers associated with meat quality traits and reproductive traits in animals. The PRKAG3 gene is highly conserved among species and animals, and it is expected that the different alleles disclosed herein will also correlate with variability in this gene in other economic or meat-producing animals such as bovine, sheep, chicken, etc.

To achieve the objects and in accordance with the purpose of the invention, as embodied and broadly described herein, the present invention provides the discovery of alternate genotypes which provide a method for screening animals to determine those more likely to possess favorable meat quality traits or to select against pigs which have alleles indicating less favorable meat quality traits. As used herein "favorable meat quality trait" means a significant improvement (increase or decrease) in one of many measurable meat quality traits above the mean of a given population, so that this information can be used in breeding to achieve a uniform population which is optimized for meat quality, this may include in increase in some traits or a decrease in others depending on the desired meat characteristics. These factors which may be considered include but are not not limited to the following:

Loin Minolta Lightness (L*): The range of 43–47 units (from darker to lighter color) is acceptable, but L* of 43 is better; i.e., has higher economic value, in general in this range (this may be dependent upon market, for example in Japan darker pork is preferred).

Loin Japanese Color Score (JCS): The range of 2.5–5.0 units (from lighter to darker color) is acceptable, but JCS of 3–4 is better Loin Marbling (level of intramuscular fat): Generally, higher marbling is better as it is associated with improved meat eating quality characteristics.

Loin pH: (ultimate meat acidity measured 24 hours postmortem; this attribute is the single most important trait of pork quality);—The range of 5.50–5.80 is desirable, but 5.80 is better as it positively influences the color and (low) purge of the meat Ham Minolta lightness (L*) The range of 43–52 units is acceptable, but lower (43) is better Ham pHu: higher; i.e., 5.80, is better Drip loss or purge: the range of 1%–3% is acceptable, but lower is better These measures of meat quality are examples of those generally accepted by those of skill in the art. For a review of meat quality traits the following may be consulted: Sosnicki, A. A., E. R. Wilson, E. B. Sheiss, A. deVries, 1998 "Is there a cost effective way to produce high quality pork?", *Reciprocal Meat Conference Proceedings*, Vol. 51.

Thus, the present invention provides a method for screening pigs to identify those more likely to produce favorable meat quality, and/or those less likely to produce favorable meat quality to optimize breeding and selection techniques for the best meat quality.

Also, the invention includes a method for screening pigs to determine those more likely to produce a larger litter when bred or to select against pigs which have alleles indicating smaller litter sizes. As used herein "larger litters" means a significant increase in litter size above the mean of a given population. Thus, the present invention provides a method for screening pigs to determine those more likely to produce larger litters, and/or those less likely to produce larger litters.

Methods for assaying for these traits generally comprises the steps 1) obtaining a biological sample from a pig; and 2) analyzing the genomic DNA or protein obtained in 1) to determine which PRKAG3 allele(s) is/are present. Also included herein are haplotype data which allows for a series of polymorphisms in the PRKAG3 gene to be combined in a selection or identification protocol to maximize the benefits of each of these markers.

Since several of the polymorphisms involve changes in amino acid composition of the PRKAG3 protein, assay methods may even involve ascertaining the amino acid composition of the PRKAG3 protein. Methods for this type or purification and analysis typically involve isolation of the protein through means including fluorescence tagging with antibodies, separation and purification of the protein (i.e. through reverse phase HPLC system), and use of an automated protein sequencer to identify the amino acid sequence present. Protocols for this assay are standard and known in the art and are disclosed in Ausubel et. al. (eds.), Short Protocols in Molecular Biology Fourth ed. John Wiley and Sons 1999.

In a preferred embodiment a genetic sample is analyzed. Briefly, a sample of genetic material is obtained from an animal, and the sample is analyzed to determine the presence or absence of a polymorphism in the AMP-activated protein kinase regulatory gamma subunit (PRKAG3) gene that is correlated with either increased litter size or improved meat quality or both traits depending on the gene form.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In a preferred embodiment the polymorphism is a restriction fragment length polymorphism and the assay comprises identifying the pig PRKAG3 gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a PRKAG3 GENE that is either known to have or not to have the desired marker. If an animal tests positive for the markers, such animal can be considered for inclusion in the breeding program. If the animal does not test positive for the marker genotype the animal can be culled from the group and otherwise used. Use of haplotype data can also be incorporated with the screening for multiple alleles for both meat quality and/or litter size.

In a most preferred embodiment the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying a genetic marker for meat quality and/or litter size in a particular population. Male and female pigs of the same breed or breed cross or similar genetic lineage are bred, and the number of offspring (for females) and/or meat quality produced by each pig is determined. A polymorphism in the PRKAG3 gene of each pig is identified and associated with the number of offspring or meat quality. Preferably, RFLP analysis is used to determine the polymorphism.

In another embodiment, the invention comprises a method for identifying a genetic marker for meat quality and/or litter size (number born) in any particular economic animal other than a pig. Based upon the highly conserved nature of this gene among different animals is it expected that with no more than routine testing as described herein this marker can be applied to different animal species to select for meat quality or litter size (number born) based on the teachings herein. Male and female animals of the same breed or breed cross or similar genetic lineage are bred, and the number of offspring or meat quality produced by each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the Reference PRKAG3 sequence. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Opitmal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the seareh for similarity method of Pearson and Lipman, *Proc. Natl. Acad Sci.* 85:2444 (1988); by computerized implementations of these algorithms, including, but not limited to: CLUSTAL in the PC/Gene program by Intelligenetics, Mountain View, Calif.; GAP, BESTFIT, BLAST, PASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244(1988); Higgins and Sharp, CABIOS 5:151–153 (1989); Corpet, et al., *Nucleic Acids Researeh* 16:10881–90(1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Chapter Protocols in Molecular Biology*, Chapter 19, Ausubel, et al., Eds., Greene Publishing and Wiley-Interscience, New York (1995).

Unless otherwise stated, sequence identify/similarity values provided herein refer to the value obtained using the BLAST 2.0 suite of programs using default parameters. Altschul et al., *Nucleic Acids Res.* 25:3389–3402 (1997). Software for performing BLAST analyses is publicly available, e.g., through the National Center for Biotechnology-Information (http://www.hcbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (B) of 10, a cutoff of 100, M=5, N=−4, and a comparison of both strands. For amino acid sequences, the BLASTP program uses as defaults a wordlength (W) of 3, an expectation (B) of 10, and the BLOSUM62 scoring matrix (see Henikoff & Henikoff (1989) *Proc. Natl. Acad. Sci, USA* 89:10915).

In addition to calculating percent sequence identity, the BLAST algorithm also performs a statistical analysis of the similarity between two sequences (see, e.g., Karlin & Altschul, *Proc. Nalt. Acad. Sci USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservatiVe substitutions are said to have "sequence similanty" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservatve substitutions is calculated, e.g., according to the algorithm of Meyers and Miller, *Computer Applic. Biol. Sci.,* 4:11–17 (1988) e.g.. as implemented in the program PC/GENE (Intelligenetics, Mountain View, Calif. USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, ore preferably at least 70%, 80%, 90%, and most preferably at least 95%.

These programs and algorithms can ascertain the analogy of a particular polymorphism in a target gene to those disclosed herein. As stated earlier based upon the highly conserved nature of the PRKAG3 gene, (Jeon T. J., V. Armeger, C. Rogel-Gaillard, A. Robic, E. Bongcam-Rudloff et al., 2001 Genomics 72: 297–303) it is expected that this polymorphism will exist in other animals and use of the same in other animals than disclosed herein involved no more than routine optimization of parameters using the teachings herein. The porcine PRKAG3 sequence is shown in FIG. 1.

It is also possible to establish linkage between specific alleles of alternative DNA markers and alleles of DNA markers known to be associated with a particular gene (e.g. the PRKAG3 gene discussed herein), which have previously been shown to be associated with a particular trait. Thus, in the present situation, taking the PRKAG3 gene, it would be possible, at least in the short term, to select for pigs likely to produce larger litters and/or better meat quality, or alternatively against pigs likely to produce smaller litters and/or less favorable meat quality, indirectly, by selecting for certain alleles of a PRKAG3 associated marker through the selection of specific alleles of alternative chromosome 15 markers. Examples of such markers known to be linked to PRKAG3 on porcine chromosome 15 include SW1683 and SW1983. As used herein the term "genetic marker" shall include not only the polymorphism disclosed by any means of assaying for the protein changes associated with the polymorphism, be they linked markers, use of microsatellites, or even other means of assaying for the causative protein changes indicated by the marker and the use of the same to influence the meat quality of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example http://darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

The accompanying figures, which are incorporated herein and which constitute a part of this specification, illustrates one embodiment of the invention and, together with the description, serve to explain the principles of the invention.

DESCRIPTION OF THE FIGURES

FIG. 1 is a depiction of the porcine PRKAG3 nucleotide sequence (SEQ ID NO:1), including the amino acids, alternative polymorphic loci and their amino acid changes are identified.

FIGS. 2A (SEQ ID NO: 11) and 2B (SEQ ID NO:12) depict the sequence of the 5' flanking region of the PRKAG3 gene including exon 1, exon 2 and novel intron sequence in between. FIG. 2A is with SINE (11) and FIG. 2B is without SINE (22). This sequence may be used to form additional primers. Bold designates direct repeats between the SINE; bold and italic designates exons of PRKAG3 gene (exon 1 and exon 2).

DETAILED DESCRIPTION OF THE INVENTION

Figure 3A:
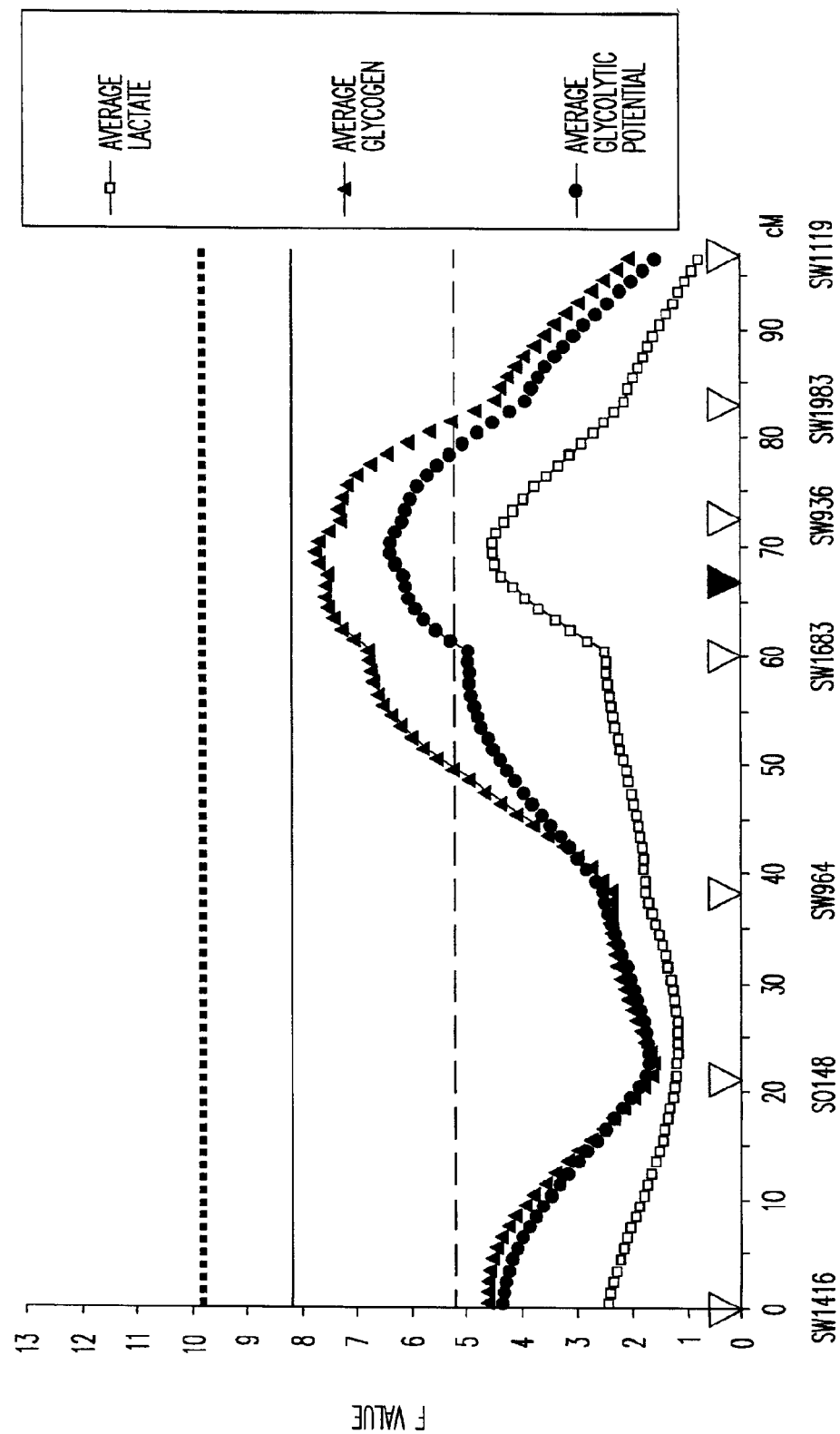
FIGS. 3a and 3b are graphs depicting F-ratio curves for evidence of QTL associated with meat quality for SSC 15. The x-axis indicates the relative position on the linkage map. They-axis represents the F-ratio. Arrows on the x-axis indicate the postiion where a marker was present. Three lines are provided for 5% chromosome-wise(- - -) , 5% genome-wise (—) and the 1% genome-wise (- - -) significance. A, average glycogen, everage lactate, and average glycolytic potential traits. 3b shows pH traits.

Reference will now be made in detail to the presently referred embodiments of the invention, which together with the following examples, serve to explain the principles of the invention.

AMP-activated protein kinase is involved in turning on ATP-producing pathways and inhibits ATP-consuming pathways. Also, it can inactivate glycogen synthase by phosphorylation. AMPK is composed of three subunits: the catalytic α chain and two regulatory subunits β and γ.

Published application WO/01/20003 to Institut National De Le Recherche Agronomique discloses variants of the PRKAG3 gene. These included a R41Q (which corresponds in this case to amino acid 200) substitution, a V40I (amino acid 199) substitution, as associated with the known RN– allele of PRKAG3. The application reports that discovery of a mutation in codon 200 in the PRKAG3 gene associated (in homozygous or heterozygous status) with high glycolytic potential in Hampshire pigs termed the RN⁻ (200Q) phenotype. The pigs with this phenotype have a low ultimate pH, a reduced water holding capacity and give a reduced yield of cured cooked ham. Analysis of different lines of pigs suggests, however, that this mutation in codon 200 arose in the Hampshire breed and occurs in very low frequency or is completely non-existent in other pig breeds. Further, as disclosed in example 5 of the PCT publication, 200Q was shown to always be present with a 199V which would suggest that the marker at position 199 does not have variation or independent value as a genetic marker from the 200Q marker.

The application WO/01/2003 identifies that the 200Q marker is associated with the unfavorable RN– mutation. The application teaches that this marker is always found together with 199V, however, 199V is also present with 200R which has better meat quality. Applicants have surprisingly found that a third combination 199I/200R has on average better meat quality that 199V/200R. In addition, the applicants have discovered that the V199I polymorphism is surprisingly associated with variation in litter size. This information allows the 199 marker to be utilized as a breeding tool.

Still further, applicants have identified a new polymorphic loci, G52S which is associated with improved meat quality. Finally haplotype analysis was performed to assess the interaction among 199I-52G- and the known 30T polymorphism (disclosed in Milan et. al., 2000). According to this embodiment, the 30T-52G-199I haplotype (hereinafter haplotype 3) was the most favorable for meat quality traits.

FIG. 1 depicts the PRKAG3 gene and all of polymorphisms discussed herein. (SEQ ID NO:1 is the wildtype). Prior to the work described in this application, there was no evidence for this gene influencing economic traits in other breeds. Surprisingly, new markers in the PRKAG3 gene, PRKAG3-199, PRKAG-30, and PRKAG3-52, have now been found to correlate with variation in meat quality traits as well as in reproductive traits such as litter size in many breeds of pigs other than the Hampshire breed. These new markers have now been shown to correlate with meat of the highest technical quality in terms of color, pH level, marbling, and drip loss and also with the triat litter size. According to this invention, the association of these polymorphisms with these trait(s) enables genetic markers to be identified for specific breeds or genetic lines to identify animals with favorable meat characteristics and/or litter size early in the animal's life.

The different marker genotypes of PRKAG3-199 within the PRKAG3 gene that results in a guarnine to adenine transition at numbleotide position 595, (SEQ ID NO:7) resulting in a change of the amino acid valine to isoleucine (amino acid number 199) (SEQ ID NO:8). This transition in turn generates a restriction site in allele 1 associated with lower glycogen, lactate and glycolytic potential. This site was also found to correlate with increased litter size when at least one copy was present.

The different marker genotypes of PRKAG3-52 result from a polymorphism within the PRKAG3 gene that results in a guanine to adenine transition at nucleotide position 154 (SEQ ID NO:5 (amino acid 52), resulting in a transition of the amino acid glycine to serine (SEQ ID NO:6). This change in turn generates a restriction site such that allele 2 is associated with lower glycogen, lactate and glycolytic potential.

The different marker genotypes of PRKAG3-30 results from a polymorphism within the PRKAG3 gene that results in a transversion of adenine to cytosine at nucleotide position 89 SEQ ID NO:3 (amino acid 30), resulting in an amino acid change of asparagine to threonine SEQ ID No:4. This polymorphism was previously reported but not found to be correlated with any meat quality phenotype. The threonine was significantly associated with improved meat quality.

The invention relates to genetic markers for economically valuable traits in animals. The markers represent alleles that are associated significantly with a meat quality trait and/or litter size, a reproduction trait, and thus provides a method of screening animals to determine those more likely to produce a larger litter or better meat quality (or both) when bred by identifying the presence or absence of a polymorphism in the PRKAG3 gene that is so correlated.

Thus, the invention relates to genetic markers and methods of identifying those markers in an animal of a particular breed, strain, population, or group, whereby the female animal is more likely to produce a litter that is significantly increased in size (number) above the mean for that particular breed, strain, population, or group. Similarly the method may be used to identify animals that are more likely to yield meat of preferred meat quality.

Any method of identifying the presence or absence of this marker may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of the PRKAG3 gene, or other linked sequences of the PRKAG3 gene. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W. H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the PRKAG3 gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool) If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 $\mu$l of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 $\mu$l of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty $\mu$l of a 20 mg/ml solution of proteinase K and 150 $\mu$l of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 $\mu$l of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or Thermus thermophilus (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, E. coli DNA polymerase I or its Klenow fragment, T4 DNA polymerase, Tth polymerase, and Taq polymerase, a heat-stable DNA polymerase isolated from Thermus aquaticus and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., Genomics 4:560–569 (1989). The ligation amplification reaction (LAR) utilizes amplification of specific DNA sequence using sequential rounds of template dependent ligation as described in Wu, supra, and Barany, Proc. Nat. Acad. Sci. 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501–527 (1986), and Myers et al., in Genomic Analysis, A Practical Approach, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-strand Conformation Polymorphism Analysis

Target sequences or alleles at the PRKAG3 locus can be differentiated using single-strand conformation polymorphism analysis, which identifies base differences by alteration in electrophoretic migration of single stranded PCR products, as described in Orita et al., Proc. Nat. Acad. Sci. 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212–222 (1991). In another method, differences between target sequences can be detected by enzymatic cleavage of mismatched base pairs, as described in Nelson et al., Nature Genetics 4:11–18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with PRKAG3 polymorphisms.

Non-gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at www.twt.com.

Non-PCR Based DNA Diagnostics

The identification of a DNA sequence linked to PRKAG3 can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and e, e', 5, 5'-5354amethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where PRKAG3 resides, and thus defining a genetic marker linked to PRKAG3, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferrable to use combinations of markders giving specific haplotypes. Additional enzymes, constructed probes and primers can be determined through routine experimentation, combined with the teachings provided and incorporated herein.

According to the invention, polymorphisms in the PRKAG3 gene have been identified which have an association with meat quality and litter size. The presence or absence of the markers, in one embodiment may be assayed by PCR RFLP analysis using the restriction endonucleases and amplification primers may be designed using analogous human, pig or other related genes to PRKAG3 due to the high homology in the region surrounding the polymorphisms, or may be designed using known PRKAG3 gene sequence data as exemplified in GenBank or even designed from sequences obtained from linkage data from closely surrounding genes based upon the teachings and references herein. The sequences surrounding the polymorphism will facilitate the development of alternate PCR tests in which a primer of about 4–30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), "Short Protocols in Molecular Biology, Fourth Edition" John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the PRKAG3 gene is present. Preferably, RFLP analysis is performed with respect to the pig PRKAG3 gene, and the results are compared with a control. The control is the result of a RFLP analysis of the pig PRKAG3 gene of a different pig where the polymorphism of the pig PRKAG3 gene is known. Similarly, the PRKAG3 genotype of a pig may be determined by obtaining a sample of its genomic DNA, conducting RFLP analysis of the PRKAG3 gene in the DNA, and comparing the results with a control. Again, the control is the result of RFLP analysis of the PRKAG3 gene of a different pig. The results genetically type the pig by specifying the polymorphism in its PRKAG3 genes. Finally, genetic differences among pigs can be detected by obtaining samples of the genomic DNA from at least two pigs, identifying the presence or absence of a polymorphism in the PRKAG3 gene, and comparing the results.

These assays are useful for identifying the genetic markers relating to meat quality, as discussed above, for identifying other polymorphisms in the PRKAG3 gene that may be correlated with other characteristics, such as litter size and for the general scientific analysis of pig genotypes and phenotypes.

The genetic markers, methods, and novel alleles of the invention are also useful in a breeding program to improve meat quality and/or reproductive efficiency (litter size) in a breed, line, or population of pigs. In some situations continuous selection and breeding of sows that are at least heterozygous and preferably homozygous for a polymorphism associated with favorable meat quality would also lead to improvement in litter size. This would apply in the populations studied in Example 2.

The examples and methods herein disclose certain genes which have been identified to have a polymorphism which is associated either positively or negatively with a beneficial trait that will have an effect on meat quality/litter size for animals carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

EXAMPLE 1

Abstract

Several quantitative trait loci (QTL) affecting muscle glycogen content and related traits were mapped to pig chromosome 15 using a three-generation intercross between Berkshire x Yorkshire pigs. Based on the QTL location the PRKAG3 (protein kinase, AMP activated, $\gamma_3$ subunit) gene was considered to be a good candidate for the observed effects. Differences in the PRKAG3 gene sequences of the founder animals of the intercross were analyzed. The $RN^-$ mutation previously reported was not present in the cross but three missense substitutions and a polymorphic Short Interspersed Element (SINE) were identified. To confirm the hypothesis that at least one of these mutations was associated with differences in meat quality over 1,800 animals from several unrelated commercial lines were genotyped for the candidate substitutions and an association study was performed. The results demonstrate the presence of new economically important alleles of the PRKAG3 gene affecting the glycogen content in the muscle and the resulting meat quality. Haplotype analysis was shown to resolve the effects of PRKAG3 more clearly than analysis of individual polymorphisms. Because of their prevalence in the more common commercial breeds, the potential implications for the pig industry and consumers are considerably larger than the original discovery of the $RN^-$ mutation. Furthermore, these results illustrate that additional alleles of genes involved in major mutations may play a significant role in quantitative trait variation.

The recent discovery (Milan et al., 2000) of a non-conserved substitution in the PRKAG3 gene has explained the dominant mutation (denoted $RN^-$) which accounted for large differences in meat quality and processing yield in the Hampshire pig breed (LeRoy et al., 1990; Monin and Sellier, 1985). This substitution (R200Q) in the PRKAG3 gene caused a 70% increase in glycogen in muscle in $RN^-$ homozygous and heterozygous animals that then resulted in the observed lower muscle pH 24 hrs after slaughter, reduced water holding capacity in the muscle and much lower yield of a cured cooked ham product. The 200Q allele is associated with all RN animals and was present in a very high percentage of Hampshire pigs but not in pigs with an $rn^+$ phenotype or in other breeds (Milan et al., 2000 and this study).

Mammalian AMP-activated protein kinase (AMPK), plays a key role in regulating energy homeostasis in eukaryotes (Hardie et al., 1998). It consists of a catalytic subunit ($\alpha$) and two regulatory subunits ($\beta$ and $\gamma$). Two isoforms have been identified for both the $\alpha$ and $\beta$ subunits and there are three isoforms reported for the $\gamma$ subunit in several mammals (Stapleton et al., 1996, 1997; Gao et al., 1996; Milan et al., 2000). The $\gamma 3$ peptide, encoded by PRKAG3 gene, is one of three options for the $\gamma$ regulatory subunit of AMPK. When eukaryotic cells are subjected to environmental or nutritional stress factors and the AMP/ATP ratio rises significantly, then the "AMPK cascade" is induced initiating measures to conserve energy (Thorton et al., 1998) and induce the ATP synthetic pathways (Hardie et al., 1998).

The identification of QTL for meat quality traits in the region of PRKAG3 gene in an rn+resource population (Malek et al., 2001) suggested that new allelic variation in this gene may be responsible for the observed effects. In this paper we report the presence of new economically important alleles of the PRKAG3 gene affecting the glycogen content in muscle and in general the meat quality traits of pigs which include ultimate pH and color measures and which are correlated with water holding capacity, drip loss, tenderness, and cooking loss (Sellier, 1998). Initial estimates of the allelic and haplotype effects and frequencies suggest that these alleles may have significant economic potential for the pig industry and ultimately for consumers in terms of improved pork quality.

Material and Methods

Figure 3B:
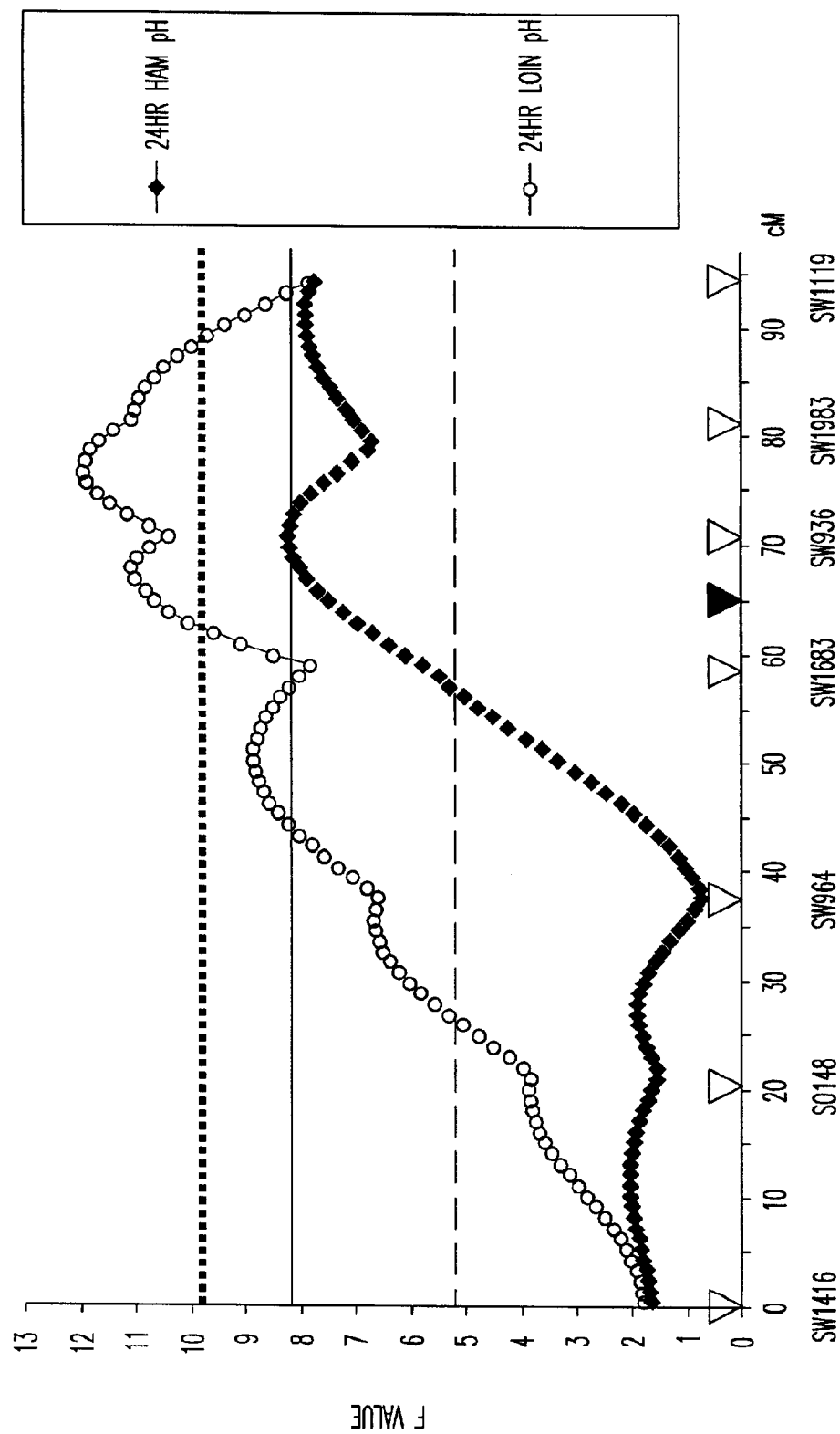

Pedigree, linkage and QTL mapping: We have generated an intercross between Berkshire and Yorkshire (B×Y) pig breeds yielding 525 $F_2$ offspring and used this pedigree to map QTL for meat quality (Malek et al., 2001) using an interval mapping method (Haley et al., 1994). In this cross, the Berkshire breed was chosen as it is regarded as having very good meat quality, particularly in terms of pH, color, water holding capacity and tenderness. The PRKAG3 gene was mapped to the BxY family linkage map using the CRI-MAP (version 2.4) mapping program (Green at al., 1990). The interval mapping method (Haley et al., 1994) including the PRKAG3 site information was used to map the QTL for meat quality for pig chromosome 15 (SSC 15) (FIG. 3). The QTL effects were estimated and represent the average Berkshire allelic effect compared to the average Yorkshire allelic effect.

Tissue Samples and DNA/RNA Isolation: Blood samples and phenotypes were collected and recorded on the $F_0$, $F_1$ and $F_2$ animals from the intercross family (Malek et al., 2001) together with blood samples and muscle tissue from ham and loin area from several $F_3$ animals. We also obtained a large collection of blood samples from five different commercial lines of pigs (Landrace, Large White, Duroc, Duroc Synthetic and Berkshire). Genomic DNA was isolated from whole blood by standard salting out procedures and total RNA was extracted from ham and loin muscle tissue using the TRIzol reagent method according to manufacturer instructions (GIBCO/BRL, Rockville, Md.).

PCR, RT-PCR, RACE and Polymorphism Discovery: Based on PRKAG3 pig gene sequence available in GenBank (AF214521), we designed primers to amplify the entire coding regions of the PRKAG3 gene. The PCR reactions were performed using 12.5 ng of porcine genomic DNA, 1.5 mM $MgCl_2$, 0.125 mM dNTP, 0.3 $\mu$M of each primer and 0.35 U Taq DNA polymerase (Promega, Madison, Wis.) and PCR buffer (10 mM Tris-HCl, 50 mM KCl, and 0.1% Triton® X-100) in a 10-$\mu$l final volume. The reverse transcription of total RNA (3.5 $\mu$g) was performed by random hexanucleotide priming and Superscript II (GIBCO/BRL, Rockville, Md.) according to the manufacturer's protocol (primers: Set A, forward 5'ATGAGCTTCCTAGAGCAAGGAG 3' (SEQ ID NO:13) and reverse 5'CAGGTCTCAATCTTATGTTCTTC 3' (SEQ ID NO:18); set B, forward 5'CGTCCGAGCGGCACCTTTGT 3' (SEQ ID NO:19), and reverse 5' AAGGTTCCAAGGTTCTCAGGC 3' (SEQ ID NO:20)). The 5' Rapid Amplification of cDNA Ends (RACE) experiments were performed using FirstChoice RLM-RACE kit (Ambion, Austin, Tex.) according to the manufacturer's instructions followed by sequencing of the PCR products (gene specific primers: outer 5'CCCACGAAGCTCTGCTTCTT 3' (SEQ ID NO:17), and inner 5'TCCTGCTCTAGGAAGCTCAT 3' (SEQ ID NO:21)). The amplicons were sequenced using dye terminators (PE Applied Biosystems, Foster City, Calif.) on an ABI 377 automated sequencer. We used Sequencher software (Gene Codes Corporation, version 4.0.5, Ann Arbor, Mich.) to assemble the sequences and to identify polymorphisms.

Genotyping and PCR-RFLP analysis: This region flanking each analyzed missense mutation was amplified using the same pair of primers for the T30N and G52S substitutions (forward 5' ATGAGCTTCCTAGAGCAAGGAG 3' (SEQ ID NO:13) and reverse 5' GGCTGCATGATGTTATGTGCCT 3' (SEQ ID NO:14)) and a different pair for I199V (forward 5'GGAGCAAATGTGCAGACAAG 3' (SEQ ID NO:16) and reverse 5'CCCACGAAGCTCTGCTTCTT 3' (SEQ ID NO:17)). After digestion with BsaHI (for I199V) HphI (for G52S) and StyI (for T30N) restriction enzymes, the digested PCR products were separated on 4% NuSieve agarose (FMC, Rockland, ME gels and stained with ethidium bromide. For the SINE polymorphism, PCR amplification (primers: forward 5'GAAACTCTTCTCCCCACAGAC 3' (SEQ ID NO:15) and reverse 5'GGCTGCATGATGTTATGTGCCT 3' (SEQ ID NO:14)) was followed by separation of the products on a 1% agarose (AMERESCO, Solonm OH) gel. After genotyping for these polymorphisms, all the animals with haplotye 2 (Table 6) were also genotyped for the R200Q substituton in order to increase the chance of finding the RN or 200Q allele (see Milan et al;, 200). Two homozygotes for the 200Q allele and four carriers were found and these were removed from further statistical analyses so that the RN mutation did not affect our analysis of the other substitutions. For the R200Q substitution we used the same primers as for the I199V mutation and the digestion was performed with the BsrBI restriction enzyme. As a final check, a random sample of about 100 animals with different haplotypes was also scored for the R200Q substitution, but none of animals carried the 200Q allele.

Phenotypic Trait Measurement: Phenotypic measures for the BxY family were made using typical industry techniques (Malek et al., 2001) and included pH, color, and glycolytic potential. For the pigs from five commercial lines, data were collected at a commercial packing plant and individual meat color (loin and ham reflectance—lower values preferred) and individual loin and ham pH 24 hours after harvest (higher values preferred) were obtained. For the packing plant data no measures of glycogen or glycolytic potential were obtained. The measures of color and pH phenotypic traits are common industry measures of meat quality that are indirectly correlated with glycogen and glycolytic potential.

Statistical Analysis

Berkshire x Yorkshire $F_2$ Population Analysis.

Associations between the PRKAG3 I199V substitution and glycogen, lactate, glycolytic potential and meat quality traits in the B×Y $F_2$ population were tested using general linear models procedures (SAS® procedure GLM, SAS Institute Inc., Cary, N.C.) with a model that included dam, slaughter date, sex and I199V genotype. Least squares means for all three genotypes were obtained for the I199V substitution.

Commercial Lines Analyses. The associations between the PRKAG3 polymorphisms and meat quality traits were tested using mixed model procedures (SASO procedure MIXED, SAS Institute Inc., Cary, N.C.) with a model which always included sire as a random effect and slaughter date and marker genotype(s) as fixed effects. Line was added as a fixed effect for across line analyses. Sex and farm were not included because all traits were measured on females only and no more than one farm was represented on each slaughter date. While males were not used in this portion of the analysis our results in the B×Y suggest no sex by genotype effect. A full model including a separate genotype effect for each of the three substitution sites was fitted across the five commercial lines. Non-significant genotype effects were removed by backwards elimination (p to remove >0.10) to identify which substitutions were associated with effects on the meat quality traits.

Least Squares (LS) means for the three genotype classes were obtained within the commercial lines for each of the substitutions analyzed individually. No line by genotype interactions were found and therefore, to improve the reliability of the estimates of the allele effects, the data from five lines were pooled for an across lines analysis.

The combined effects of the three substitutions were estimated as haplotype substitution effects. Contrasts between haplotypes were estimated from a model including sire (random), slaughter day and one variable for each haplotype with values −1, 0 and 1 corresponding to the animal having 0, 1 or 2 copies of the haplotype in question. The haplotype substitution effects were presented as deviations from the mean of the haplotypes and reflect the differences from the worst to the best haplotype. The number of animals used in association analyses varied based on the trait measured, and are listed in Tables 3, 4 and 5.

Results

Marker Development and linkage Mapping: Several significant QTL were detected on SSC15 (Malek et al., 2001) in the region where the PRKAG3 gene was located (Milan et al., 2000), between the markers SW1683 and SW1983 (FIG. 3). These included QTL for average glycogen content and glycolytic potential which have been reported (Milan et al., 2000) to be affected by the PRKAG3 200Q allele as well as the traits 24 hr ham and loin pH and 24 hr loin Hunter L values (light reflectance). The favorable allele at this QTL, which interestingly, has an additive effect (the RN⁻ mutation is dominant) was derived predominantly from the Berkshire breed (generally regarded as having very good meat quality) as expected (Table 1). The PRKAG3 gene was the unique candidate gene in this area, based on the recent development of the BAC contig in the porcine RN region (Milan et al., 2000), the high degree of linkage order conservation of the porcine map in this area with the human transcript map (Jeon et al., 2001) and the recently developed human genome map (Lander et al, 2001). We first tested the founder animals, two Berkshire sizes and nine Yorkshire dams, for the published RN⁻ substitution (R200Q). All the founder animals had the rn⁺ allele (200R). By sequencing the entire coding region of the PRKAG3 gene in B×Y family founders and in four $F_3$ individuals with extreme values for meat quality, we identified three missense mutations. These are the T30N and the I199V substitutions previously described (Milan et al., 2000) and a new missense mutation (G52S). Another non-synonymous substitution (P53L) found by Milan et al. (2000) was not found to be segregating in the founders of the B×Y family where they were all 53P. Due to the lack of information on the 5'UTR, we used RACE in order to find the complete 5'flanking sequence and gene organization in that region. An intronic SINE polymorphism was discovered starting 79 bp upstream of the start codon but this was present only in three Yorkshire grandams. Based on the differences in allele frequency of each site between the founders of the intercross family, we considered the G52S and I199V substitutions as the most likely candidates for the meat quality QTL reported previously. Using the I199V substitution we mapped the PRKAG3 gene in the B×Y linkage map to a position below the broad peak(s) of the QTL for glycogen, lactate and glycolytic potential and 24 hr pH (FIG. 3). After adding the PRKAG3 I199V information the map length and marker order on SSC 15 was the same as in Malek et al. (2001). Re-analysis of the QTL including PRKAG3 I199V (FIG. 3) caused small changes in the F value and the location of the QTL peaks on SSC 15 (from 0 to 3 cM) when compared with the results of Malek et al. (2001).

$F_2$ Association Study: Using an association analysis, we found significant effects of all three of the substitutions (T30N, G52S and I199V) on average glycogen and lactate content and also on glycolytic potential on the $F_2$ B×Y population (data shown only for I199V substitution—Table 2). The most significant effects were revealed for I199V substitution for most of the traits analyzed, including glycogen and lactate content and glycolytic potential measures, but also in some of the meat quality traits associated with these measures. From the $F_2$ data, the 30T, 52G and 199I alleles were favorable in terms of meat quality. Given the large expected linkage disequilibrium in the intercross it was necessary to investigate and confirm the effects of these mutations in several outcross commercial lines of pigs in order to determine whether this gene is likely to be directly involved in the observed variation in meat quality.

Analysis of Commercial Populations: The genotypic frequencies for the analyzed substitutions are presented in Table 3. For all three substitution sites, the Berkshire line had a higher frequency for the genotypes associated with low glycogen content (and higher meat quality) in skeletal muscle based on the B×Y $F_2$ data. The other commercial populations have lower frequencies of the favorable alleles with this being particularly marked for the I199V substitution when compared with the Berkshire population.

The PRKAG3 mutations and their associations with meat quality were tested for each of the five commercial lines and also across all of the lines. Backwards elimination of substitution sites, in the across lines analysis, kept I199V in the model for all six traits, G52S for ham pH, loin pH, loin Minolta L and loin Minolta b and T30N was kept for ham Minolta L, loin Minolta L and ham Minolta b.

Because each of the substitutions showed distinct associations with at least three of the traits, the effects of each of the substitutions were estimated independently. Least square estimates of the genotype means across lines (Table 4) and within line (Table 5) showed significant effects between the analyzed substitutions and measures of meat quality, suggesting that several additional (new) rn⁺ alleles may exist.

The association study revealed that the largest effects across the lines (Table 4) and also within lines (Table 5, data shown only for I199V) were obtained with the I199V substitution for all the traits analyzed. For this substitution the associations were highly significant (p<0.0005) for all of the meat quality traits used in this study when analyzed across Lines. Significant associations with at least one of the traits were revealed for the same substitution within each of the individual lines, with highly significant effects for ham Minolta b in Duroc and Duroc synthetic and for loin pH in Duroc Synthetic. These two breeds (Duroc Synthetic, Duroc) have the best frequency distribution for association analysis with a sufficient number of animals for each genotype (Table 5). In the across lines analysis and most of the individual line results, the effects were in the same direction for all traits with allele 199I being the favorable allele for high meat quality.

Significant effects, but smaller when compared to the I199V, were revealed for the T30N substitution in five of the traits when analyzed across lines (Table 4). Within line analyses of T30N revealed effects almost exclusively in Duroc and Duroc Synthetic populations (data not shown). In most of the situations, the effects were in the same direction, the allele 30T being associated with a better meat quality.

For the G52S substitution, significant (p<0.05) effects were identified for only two of the traits (ham pH and loin Minolta L) in across lines analysis, and a different allele was identified as favorable for those traits. Within line analysis revealed significant associations for just the Duroc Synthetic population for loin Minolta color scores (data not shown).

In the five commercial populations we tested, we found just four haplotypes (Table 6). The Berkshire population is the least polymorphic, having haplotype 3 (30T-52G-199I) at a high frequency (0.87). In Large White haplotype 2 (30T-52S-199V) is the most frequent and haplotype 1 (30N-52G-199V) has the highest frequency in Landrace, Duroc and Duroc Synthetic populations. Haplotype 4 (30T-52G-199V) has the lowest frequency in all the populations.

Figure 4:
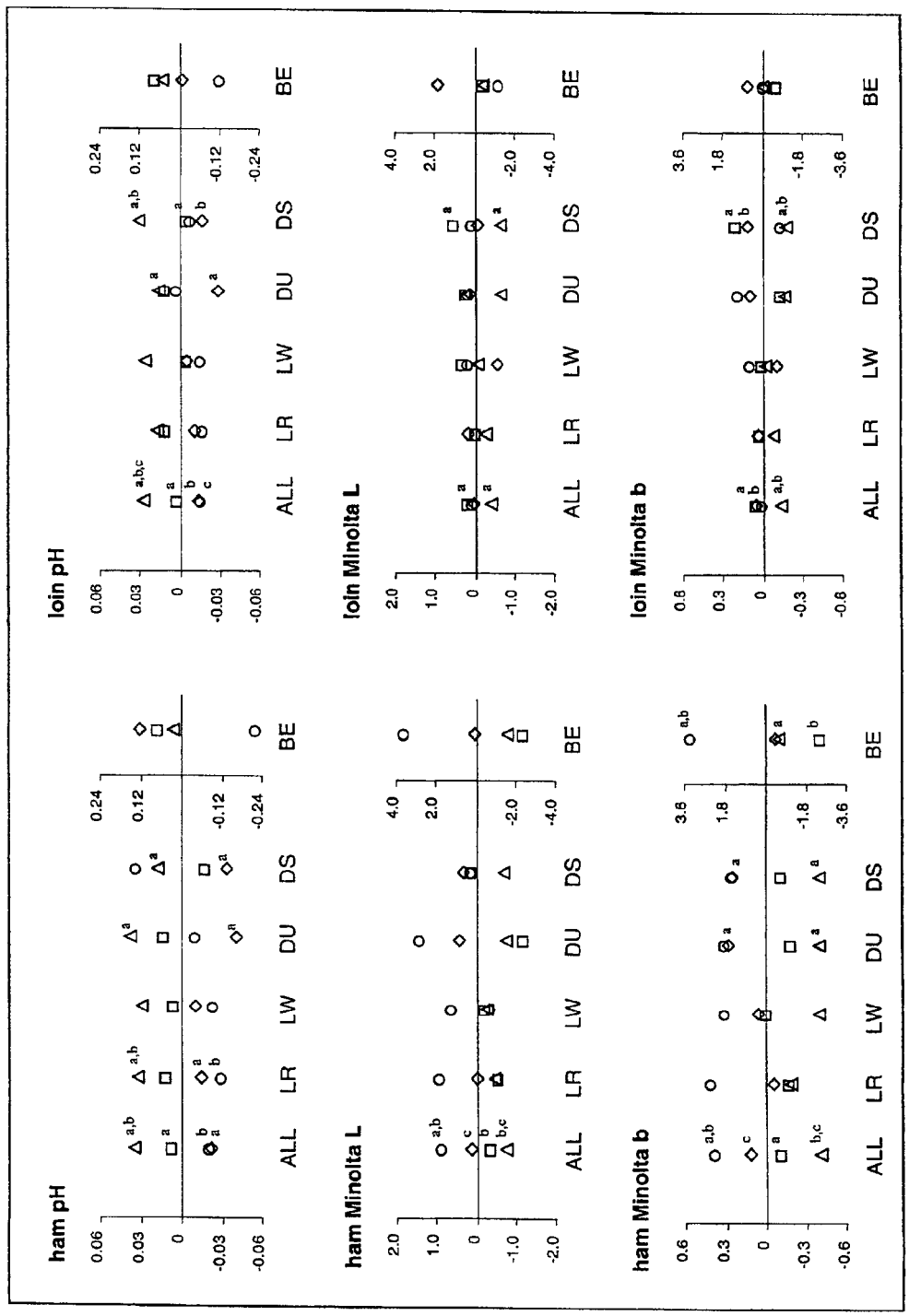
FIG. 4 demonstrates haplotype substitution effects of PRKAG3 on pH and color scores in the ham and loin. Haplotype substitution effects are estimated across 5 lines (ALL)and within each line. Lines are based on Landrace (LR), Large White (LW) or Duroc (DU), a Duroc based synthetic line (DS) and a Berkshire basede line (BE). A separate scale is used for the BE line. Estimates within a column that have the same superscropt are significantly different at p<0.005 for the across lines estimates and tat p<0.005 for the within line estimates.

The haplotype substitution effects for each line arid across lines were calculated as the deviation from the average of the four haplotypes (FIG. 4). Across and within line analyses showed bigger differences between haplotypes for ham pH and color measurements than for traits of the loin. For ham pH, across and within line analyses showed haplotype 3 having the highest effect which was significantly different from each of the other haplotypes in the across lines analysis (p<0.0005) and from at least one other haplotype in each individual line analysis (p<0.05). Haplotype 2 was the next best for most of the traits and lines with haplotypes 1 and 4 tending to be the worst with respect to meat quality. This hierarchy is not evident in the Berkshire population, where significant differences are only seen with haplotype 4 which has the lowest value, corresponding to the across lines result. The non-significant results in Berkshire are likely to be due in part to the low level of polymorphism in this breed and the concomitant very low number of observations for haplotypes 1 and 4. The estimate for haplotype 4 in the Duroc Synthetic population appears to be different to that in the other lines (especially for ham pH where it is significantly higher than haplotype 2 (p<0.05) and haplotype 1 (p<0.01), but the frequency of haplotype 4 in this population was very low (0.07). The synthetic nature of this line (though its inception was six generations ago) also provides the opportunity for extended linkage disequilibrium to be present, increasing the chance for linked loci to contribute to the haplotype substitution effects.

The haplotype results for Minolta scores were in line with the pH results. Haplotype 3 was generally found to have the favorable effect (lower color scores). There are a few exceptions in the results from individual lines and these may be the result of sampling. The only significant deviation is with haplotype 2, which is associated with a lower Minolta b score in Berkshire (p<0.05). In the across line analysis haplotype 2 was second to haplotype 3 in most cases.

Discussion

The results reported in this work provide important evidence in favor of the presence of new alleles of the PRKAG3 gene affecting meat quality traits. This conclusion is based on three points: 1) the known effect of PRKAG3 alleles, rn$^+$ and RN$^-$ on meat quality. 2) observation of several QTL for related meat quality traits discovered on SSC15 in the region where PRKAG3 is located in the B×Y family. These QTL were discovered in this pig cross where the original R200Q substitution was not segregating and 3) results presented here on the association between the PRKAG3 substitutions and glycogen and lactate content, glycolytic potential and meat quality traits in the B×Y F2 population and with meat quality traits in several unrelated commercial pig lines.

Association analyses of the individual substitutions revealed that, of the three studied here, the I199V substitution showed the most significant and largest differences in meat quality traits. For example, B×Y $F_2$ analysis showed significant differences between the I199V genotype classes for glycolytic potential, but also in glycogen and lactate content (Table 2). Important effects were also revealed for most of the meat quality traits analyzed. Allele 199I was found to be associated with a lower level of glycogen, lactate and glycolytic potential, higher ham and loin pH and with better color scores. This marker was sufficiently informative in B×Y $F_2$, to provide good estimates of the allele effects.

In the analyses of the commercial populations, the I199V substitution is associated with significant differences in LS means between the homozygous classes up to 0.14 in the Landrace line and 0.10 across the lines for ham pH (Tables 4 and 5). For one of the meat color measures, Ham Minolta L, significant LS means differences were found between homozygous genotypes up to 3.5 units of reflectance (in Landrace) and 2.0 across the lines. These effects are in the range of 0.5 to 1 phenotypic standard deviation. Important differences were also revealed for the other traits and breeds. Effects of this magnitude in traits important for overall meat quality are of great interest to the animal breeding industry.

Besides I199V, large effects were also estimated from single substitution analysis of T30N. However, only modest effects of the T30N substitution remained if I199V was also included in the analysis. Strong linkage disequilibrium between sites 30 and 199, is considered to be in large part responsible for the effects being detected for site 30. Small effects, which were mostly non-significant, were observed for the single site analysis of G52S.

Haplotype analysis helped to dissect the effects of the non-synonymous substitutions and provided additional evidence for an effect at position 199 as well as 52. Haplotype 3, which is the only haplotype containing 199I, was the most favorable haplotype with respect to pH and meat color measurements. In most of the situations tested, haplotype 2, which is the only haplotype containing 52S, showed an intermediate value, especially for ham quality traits where the differences in effects were more significant and bigger than in other traits. Values for haplotypes 1 and 4 are close together at the bottom of the range and in most cases not significantly different from each other.

The observation that the values of these two haplotypes (1 and 4) are relatively similar for most estimates makes us conclude that the T30N substitution is only making a marginal contribution to meat quality variation. In across line, Landrace and Large White analyses, where the frequency of the haplotype 4 is above 0.10, we find a favorable effect of haplotype 1 on ham Minolta scores (this haplotype being associated with the 30N variant) when compared with haplotype 4. In the other populations, differences between these haplotype effects are poorly estimated due to very low frequency of the haplotype 4.

The difference between haplotype 4 and haplotype 2 is only at the G52S site. The effects of haplotype 4 and 2 are significantly different for pH and Minolta L scores in both ham and loin in the across lines analysis and for several traits of the individual lines, most notably the Large White. Haplotype 2 (which contains 52S and encodes a serine) is favorable over haplotype 4 (which contains 52G and encodes a glycine). This is the opposite of what was found in the B×Y study where 52G was predicted to be the favorable allele. Strong linkage disequilibrium with the I199V site, due to the limited number of founders of the $F_2$, may have masked the true effect of the G52S substitution in this population. Interestingly, the individual analysis of G52S did not show any effect for most traits and lines. That analysis compares haplotype 2 with the other three combined. It can be seen from FIG. 4 that a mixture of the other three haplotypes can, depending on haplotype frequencies, result in a mean value close to that of haplotype 2 so that a difference would not be detected when G52S is analyzed individually, which points out the value of haplotype based analysis.

The 30T variant, present in haplotype 4, was found to be favorable for meat quality based on the single site analysis, being associated with significant effects in the Duroc and Duroc Synthetic lines for most of the traits. In these two populations haplotype 3 has a moderate frequency (Table 6) and contains both the 30T and the favorable 199I variant. Thus the 199I variant contributes to the higher effects for the 30T site variant due to linkage disequilibrium.

We conclude that the joint analyses of substitutions and the haplotype analyses demonstrate the presence of three non-synonymous substitutions in the PRKAG3 gene with different size effects on meat quality measurements in pigs. This interesting model of "one gene—several polymorphisms-diverse phenotypes" is based on distinguishable additive effects on a complex phenotypic trait and can serve as a model for future studies with other traits. The presence of multiple alleles as a consequence of consecutive mutations in a gene under selection has also been proposed recently in pigs (Jeon et al., 1999; Nezer et al., 1999)

The I199V substitution is in a cystathionine beta-synthase (CBS) domain, a very conserved region in genes of this family (Milan et al., 2000). The role of the CBS domain is still unclear but it is suggested to be involved in cytoplasmic targeting (Pontig, 1997), protein-protein interaction (Bateman, 1997) and/or regulation (Bateman, 1997) of protein activity. There are four CBS domains in the PRKAG3 gene (Milan et al., 2000) and the I199V substitution is located in the first and most conserved domain. Alignment between the CBS domain and the $\gamma_3$ peptide obtained using Pfam software, revealed that the preferred amino acid at this position is isoleucine (result not shown). Interestingly in this study, allele 199I (coding isoleucine at the site 199) was found to be associated with better meat quality in commercial populations and the B×Y $F_2$ family and also in lower levels of glycogen, lactate and glycolytic potential in the latter one.

Milan et al. (2000) show that the 200Q variant (RN⁻) is always found with 199V. However, 199V is found with both 200R and 200Q and 199I is always found with 200R. As only three nucleotides separate these substitution sites, the probability of recombination between them is extremely small. For this reason we can consider R200Q to be the most recent substitution, a hypothesis also supported by the presence of this mutation only in the Hampshire pig breed. Both of the haplotypes 199V-200R and 199I-200R could be ancestral, because each has been identified in most of the breeds analyzed to date (Milan et al., 2000) including wild boar and several species of suborder *Suisformes* (Ciobanu et al., unpublished results).

The 199V-200R haplotype is associated with higher glycogen content and lower post mortem ham/loin pH when compared with the 199I-200R haplotype (B×Y F2 data). The substitution at codon 199 presumably leads to an effect on glucose metabolism and therefore an increase in the muscle glycogen content. The third haplotype 199V-200Q confers the RN⁻ phenotype. The associated effect 199V-200Q on glycogen content is larger than the effect of other haplotypes and the 199V-200Q haplotype is dominant over the others. For these reasons we suggest that the RN⁻ phenotype could be a combined effect of the 199V-200Q haplotype rather than it being solely a result of the R200Q substitution. This effect could be caused by the modification of the CBS domain by these substitutions.

The exact functions of the β and γ regulatory subunits of the AMPK are still unclear. However, it is known that both are essential for kinase activity (Hardie and Carling, 1997). In vitro experiments show that the β subunit may have an important role in the formation of the heterotrimeric structure of AMPK, as β interacts with both of the γ and α subunits which do not interact directly with each other (Woods et al., 1996). Recent evidence suggests that the allosteric AMP-binding site may involve both γ and α subunits of the AMPK complex (Cheung et al., 2000). Cheung et al. (2000) proposed an elegant model in which, in the absence of AMP, the heterotrimeric complex may be predominantly inactive without interaction between the γ and α subunits. In this situation phosphorylation of the $Thr^{172}$ site in the α subunit and interaction with substrates, is blocked by the autoinhibitory region of the α subunit. In the active form of AMPK the interaction between the α autoinhibitory region and one or more of the γ CBS domains prevents the autoinhibition, and AMP binds on both subunits to stabilize the assembly (Cheung et al., 2000). The alignment information, the proposed model of the regulation of the AMPK complex and also the presence of the R200Q site nearby, supports the hypothesis of a possible role of the I199V substitution on the activity of AMPK. Even though the molecular structure of the AMPK complex has not been resolved yet, we hypothesize that the amino acid change, may also influence the structure and activity of the enzyme resulting in the observed effect of the G52S substitution.

Although the $\gamma_3$ subunit is highly expressed in skeletal muscle, AMPK activity appears to be associated more with $\gamma_1$ and $\gamma_2$ isoforms (Cheung et al., 2000). However, in a mechanism not yet understood, the R200Q substitution (or I199V-R200Q combination) in PRKAG3 gene causes important differences in AMPK activity in Hampshire pigs (Milan et al., 2000) which suggests that the $\gamma_3$ isoform has an important role in glucose metabolism in skeletal muscle. Detailed functional studies of the different subunit combinations will be necessary to resolve the situation. The role of AMPK in glucose metabolism makes physiological sense, based on comparisons with the related SNF1 complex from yeast. Also, several studies show that AMPK participates in glycogen metabolism by: inactivation of glycogen synthase (Carling and Hardie, 1989; Poulter et al., 1988; Zhang et al., 1993), activation of the nitric oxide synthase (Fryer et al., 2000) and by increasing the translocation of the glucose transporter 4 to the plasma membranes (Hayashi et al., 1998; Kurth-Kraczek et al., 1999; Bergeron et al., 1999; Holmes et al., 1999).

While the effects of the substitutions reported here on the measures of meat quality are of lesser magnitude than those of the dominant RN⁻ mutation, they are of importance both biologically and economically. In particular these alleles are segregating in all of the commercial lines and breeds analyzed to date in contrast to the RN⁻ mutation, which is associated only with the Hampshire breed and has limited use in most pork production programs. The results reported here for PRKAG3 also suggest that geneticists should look for additional mutations with an economic impact in genes known to cause more drastic effects both within and between species. This notion is supported by reports of major effects associated with other genes outside the target species or breed, e.g. large effects of MC4R mutations in mice (Huszar et al., 1997) and humans (Yeo et al., 1998) and to a lesser extent in pigs (Kim et al., 2000).

The identification of novel genes with biochemical significance in animal species will also provide useful information for human biomedical targets. This knowledge is enhanced when new and interesting alleles are discovered. In the case of PRKAG3, it has been suggested (Milan et al., 2000) that this gene, and other AMPK related genes in humans, are interesting candidates for human type II diabetes, based on their function and QTL locations. For this reason the effect of these new alleles may provide new insights about potential factors affecting glucose metabolism and should be considered in further investigations of this disease.

All references cited herein are hereby incorporated in their entirety by reference, including but not limited to the following:

Bateman, A., 1997 The structure of a domain common to archaebacteria and the homocystinuria disease protein. Trends Biochem. Sci. 22: 12–13.

Bergeron, R., R. R. Russell 3rd, L. H. Young, J. M. A. Ren, M. Marcucci et al., 1999 Effect of AMPK activation on muscle glucose metabolism in conscious rats. Am. J. Physiol. 276: E938–E944.

Carling, D., and D. G. Hardie, 1989 The substrate and sequence specificity of the AMP-activated protein kinase. Phosphorylation of glycogen synthase and phosphorylase kinase. Biochim. Biophys. Acta 1012: 81–86.

Cheung, P. C., I. P. Salt, S. P. Davies, D. G. Hardie and D. Carling, 2000 Characterization of AMP-activated protein kinase gamma-subunit isoforms and their role in AMP binding. Biochem J. 346: 659–669.

Fryer, L. G., E. Hajduch, F. Rencurel, I. P. Salt, H. S. Hundal et al., 2000 Activation of glucose transport by AMP-activated protein kinase via stimulation of nitric oxide synthase. Diabetes 49: 1978–1985.

Gao, G., S. Fernandez, D. Stapleton, A. S. Auster, J. Widmer, J. R. B. Dyck et al., 1996 Non-catalytic beta- and gamma-subunit isoforms of the 5'-AMP-activated protein kinase. J. Biol. Chem. 271: 8675–8681.

Green, P., K. Falls and S. Crooks, 1990 Documentation for CRIMAP, version 2.4., Washington University, School of Medicine, St. Louis, Mo.

Haley, C. S., S. A. Knott and J. M. Elsen, 1994 Mapping quantitative trait loci in crosses between outbred lines using least squares. Genetics 136: 1195–1207.

Hardie, D. G., and D. Carling, 1997 The AMP-activated protein kinase—fuel gauge of the mammalian cell? Eur. J. Biochem. 246: 259–273.

Hardie, D. G., D. Carling and M. Carlson 1998 The AMP-activated/SNF1 protein kinase subfamily: metabolic sensors of the eukaryotic cell? Annu. Rev. Biochem. 67: 821–855.

Hayashi, T., M. F. Hirshman, E. J. Kurth, W. W. Winder and L. J. Goodyear, 1998 Evidence for 5' AMP-activated protein kinase mediation of the effect of muscle contraction on glucose transport. Diabetes 47: 1369–1373.

Holmes, B. F., E. J. Kurth-Kraczek and W. W. Winder, 1999 Chronic activation of 5'-AMP-activated protein kinase increases GLUT-4, hexokinase, and glycogen in muscle. J. Appl. Physiol. 87: 1990–1995.

Huszar, D., C. A. Lynch, V. Fairchild-Huntress, J. H. Dunmore, Q. Fang et al., 1997 Targeted disruption of the melanocortin-4 receptor results in obesity in mice. Cell 88: 131–141.

Jeon, J. T., O. Carlborg, A. Tornsten, E. Giuffra, V. Amarger, P. Chardon, L. Andersson-Eklund, K. Andersson, I. Hansson, K. Lundstrom, and L. Andersson, 1999. A paternally expresssed QTL affecting skeletal and cardiac muscle mass in pigs maps to the IGF2 locus. Nat. Genet. 21: 157–158.

Jeon, T. J., V. Amarger, C. Rogel-Gaillard, A. Robic, E. Bongcam-Rudloff et al., 2001 Comparative analysis of a BAC contig of the porcine RN region and the human transcript map: implications for the cloning of trait loci. Genomics 72: 297–303.

Kim, K. S., N. Larsen, T. Short, G. Plastow and M. F. Rothschild, 2000 A missense variant of the porcine melanocortin-4 receptor (MC4R) gene is associated with fatness, growth, and feed intake traits. Mamm. Genome 11: 131–135.

Kluijtmans, L. A., G. H. Boers, E. M. Stevens, W. O. Renier, J. P. Kraus et al., 1996 Defective cystathionine beta-synthase regulation by S-adenosylmethionine in a partially pyridoxine responsive homocystinuria patient. J. Clin. Invest. 98: 285–289.

Kurth-Kraczek, E. J., M. F. Hirshman, L. J. Goodyear and W. W. Winder, 1999 5' AMP-activated protein kinase activation causes GLUT4 translocation in skeletal muscle. Diabetes 48: 1667–1671.

Lander, E. S., L. M. Linton, B. Birren, C. Nusbaum, M. C. Zody et al., 2001 Initial sequencing and analysis of the human genome, Nature 409: 860–921.

LeRoy, P., J. Naveau, J. M. Elsen and P. Sellier, 1990 Evidence for a new major gene influencing meat quality in pigs. Genet. Res. 55: 33–40.

Malek, M., J. C. M. Dekkers, H. K. Lee, T. J. Baas, K. Prusa et al., 2001 A molecular genome scan analysis to identify chromosomal regions influencing economic traits in the pig. II. Meat and muscle composition. Mamm. Genome (in press).

Milan, D., J. T. Jeon, C. Looft, V. Amarger, A. Robic et al., 2000 A mutation in PRKAG3 associated with excess glycogen content in pig skeletal muscle. Science 288: 1248–1251.

Monin, G. and P. Sellier, 1985 Pork of low technological quality with a normal rate of muscle pH fall in the immediate postmortem period: The case of Hampshire breed. Meat Sci. 3: 49–63.

Nezer, C., I. Moreau, L. Karim, B. Brouwers, W. Coppieters, J. Detilleux, R. Hanset, A. Kvasz, P. Leroy, and M. Georges 1999. An imprinted QTL with major effects on muscle mass and fat deposition maps to the IGF2 locus in pigs. Nat. Genet., 21: 155–156.

Ponting, C. P., 1997 CBS domains in CIC chloride channels implicated in myotonia and nephrolithiasis (kidney stones). J. Mol. Med. 75: 160–163.

Poulter, L., S. G. Ang, B. W. Gibson, D. H. Williams, C. F. Holmes et al., 1988 Analysis of the in vivo phosphorylation state of rabbit skeletal muscle glycogen synthase by fast-atom-bombardment mass spectrometry. J. Biol. Chem. 175: 497–510.

Sellier, P.,1998. Genetics of meat and carcass traits, pp.463–510 in The Genetics of the Pig, edited by M. F. Rothschild, and A. Ruvinsky. CABI, Wallingford, UK Stapleton, D., E. Woollatt, K. I. Mitchelhill, J. K. Nicholl, C. S. Fernandez et al., 1997 AMP-activated protein kinase isoenzyme family: subunit structure and chromosomal location. FEBS Lett. 409: 452–456.

Stapleton, D., K. I. Mitchelhill, G. Gao, J. Widmer, B. J. Michell et al., 1996 Mammalian AMP-activated protein kinase subfamily. J. Biol. Chem. 271: 611–614.

Thornton, C., M. A. Snowden and D. Carling, 1998 Identification of a novel AMP-activated protein kinase beta subunit isoform that is highly expressed in skeletal muscle. J. Biol. Chem. 273: 12443–12450.

Woods, A., P. C. F. Cheung, F. C. Smith, M. D. Davison, J. Scott et al., 1996 Characterization of AMP-activated protein kinase beta and gamma subunits. Assembly of the heterotrimeric complex in vitro. J. Biol. Chem. 271: 10282–10290.

Yeo, G. S., I. S. Farooqi, S. Aminian, D. J. Halsall, R. G. Stanhope et al., 1998 A frameshift mutation in MC4R associated with dominantly inherited human obesity. Nat. Genet. 20: 111–112.

Zhang, W., A. A. DePaoli Roach and P. J. Roach, 1993 Mechanisms of multisite phosphorylation and inactivation of rabbit muscle glycogen synthase. Arch. Biochem. Biophys. 304: 219–225.

The following traits were not significant at p<0.05: Lab Ham Minolta, Lab Ham Hunter, and Packing plant Loin Minolta. Least squares means were estimated for each trait and are presented with standard errors of the estimates in parenthesis. The number of animals in each genotypic class are: n=131 (II), 260–265 (IV), and 111–113 (VV). Significant differences between least squares estimates are indicated with 2-letter superscripts: a-b p<0.05, c-d p<0.005, e-f p<0.0005. An estimate with superscript "a" is significantly different from estimate(s) with superscript "b", same for c-d and e-f at their respective significance levels.

TABLE 1

Evidence for significant QTL at the 5% chromosome-wise level for various meat quality traits for pig chromosome 15.

| Trait | F-Value[a] | Location (cM) | Additive Effect[b] | S.E. | Dominance Effect | S.E. | Variance[c] (%) |
|---|---|---|---|---|---|---|---|
| Ave. Glycogen[d] | 7.74 | 69 | −0.70 | 0.21 | 0.65 | 0.031 | 3.52 |
| Ave. Lactate[d] | 4.50 | 69 | −2.24 | 0.79 | −1.10 | 1.16 | 2.00 |
| Ave. Glyoytic Potential[d] | 6.37 | 69 | −3.63 | 1.02 | 0.18 | 1.50 | 4.69 |
| 24 hr. Ham pH | 8.42* | 72 | 0.05 | 0.01 | −0.02 | 0.02 | 4.00 |
| 24 hr. Loin pH | 12.21** | 78 | 0.05 | 0.01 | −0.01 | 0.02 | 5.61 |

[a]Chromosome-wise F-statistic thresholds at the 5% level, as determined by permutation test was 5.02.
[b]Additive (a) and dominance (d) QTL effects correspond to genotype values of +a, d, and −a, respectively, for individuals having inherited two Berkshire alleles, heterozygotes and individuals with two Yorkshire alleles. Positive additive effects indicate that Berkshire alleles increased the trait, negative that the Berkshire alleles decreased it. Dominance effects are relative to the mean of the two homozygotes.
[c]% Variance = genetic variance at the QTL based on estimated additive and dominance effects and allele frequencies of ½, as a percent of the residual variance in the $F_2$.
[d]units of measure — $\mu$mol/g
*Significant at the 5% genome-wise level (F > 8.22)
**Significant at the 1% genome-wise level (F > 9.96)

TABLE 2

Association results between the genotypes at I199V substitution site of the PRKAG3 gene and meat quality traits in Berkshire x Yorkshire $F_2$ animals.

| TRAITS | II | IV | VV |
|---|---|---|---|
| Ave. Glycogen | 8.01 (0.31)[c] | 9.10 (0.24)[d] | 9.37 (0.33)[d] |
| Ave. Lactate | 84.83 (1.17)[e] | 86.83 (0.91)[a] | 90.54 (1.27)[f,b] |
| Ave. Glycolytic Potential | 100.84 (1.50)[a,e] | 105.02 (1.17)[b] | 109.28 (1.64)[f,a] |
| Packing Plant Ham pH | 5.91 (0.02)[c] | 5.89 (0.02) | 5.84 (0.02)[d] |
| Packing Plant Loin pH | 5.80 (0.02)[c,e] | 5.75 (0.01)[d,a] | 5.71 (0.02)[f,b] |
| Lab Loin pH | 5.86 (0.02)[c,e] | 5.80 (0.01)[d,a] | 5.77 (0.02)[f,b] |
| Lab Loin Minolta | 21.54 (0.29)[c] | 22.11 (0.22) | 22.76 (0.31)[d] |
| Packing Plant Loin Hunter | 44.17 (0.41)[a] | 45.07 (0.32) | 45.49 (0.45)[b] |
| Lab Loin Hunter | 46.56 (0.30)[a] | 47.07 (0.23) | 47.70 (0.33)[b] |

TABLE 3

Genotypic frequencies for the T30N, G52S and I199V substitutions in the PRKAG3 gene in five commercial pig breeds.

| SNP | Genotype | Landrace | Large White | Berkshire | Duroc | Duroc Synthetic |
|---|---|---|---|---|---|---|
| T30N | TT | 0.27 | 0.69 | 0.89 | 0.34 | 0.37 |
|  | TN | 0.50 | 0.29 | 0.11 | 0.46 | 0.48 |
|  | NN | 0.23 | 0.02 | 0.00 | 0.20 | 0.15 |
|  | n | 556 | 404 | 103 | 298 | 627 |
| G52S | SS | 0.07 | 0.19 | 0.00 | 0.02 | 0.03 |
|  | SG | 0.42 | 0.49 | 0.10 | 0.25 | 0.24 |
|  | GG | 0.51 | 0.32 | 0.90 | 0.73 | 0.73 |
|  | n | 560 | 409 | 91 | 257 | 649 |
| I199V | II | 0.02 | 0.07 | 0.74 | 0.17 | 0.14 |
|  | IV | 0.23 | 0.31 | 0.25 | 0.44 | 0.47 |
|  | VV | 0.75 | 0.62 | 0.01 | 0.39 | 0.39 |
|  | n | 569 | 375 | 89 | 260 | 578 |

TABLE 4

Association results between the genotypes at T30N, G52S and I199V substitution sites of the PRKAG3 gene and meat quality traits across five commercial pig breeds.

| TRAITS | T30N | | | G52S | | | I199V | | |
|---|---|---|---|---|---|---|---|---|---|
| | TT | TN | NN | SS | SG | GG | II | IV | VV |
| Ham pH | 5.76 (.01)[e] | 5.71 (.01)[f,a] | 5.69 (.01)[f,b] | 5.77 (.02)[a] | 5.74 (.01) | 5.74 (.01)[b] | 5.81 (.01)[e] | 5.74 (.01)[e,f] | 5.71 (.01)[f] |
| n | 461 | 506 | 176 | 76 | 378 | 659 | 128 | 376 | 559 |
| Loin pH | 5.74 (.01)[c,e] | 5.73 (.01)[d] | 5.70 (.01)[c,f] | 5.74 (.01) | 5.73 (.01) | 5.73 (.01) | 5.78 (.01)[e] | 5.74 (.01)[e,f] | 5.71 (.01)[f] |
| n | 772 | 788 | 258 | 135 | 620 | 1054 | 199 | 614 | 922 |
| Ham Minolta L | 45.9 (.25)[c,e] | 46.6 (.26)[d] | 47.2 (.36)[f] | 45.5 (.49) | 46.2 (.29) | 46.5 (.25) | 44.9 (.38)[e] | 46.5 (.27)[f] | 46.9 (.26)[f] |
| n | 462 | 509 | 176 | 76 | 379 | 662 | 128 | 376 | 561 |
| Loin Minolta L | 44.8 (.17)[a] | 44.8 (.18)[a] | 45.3 (.24)[b] | 45.6 (.30)[a] | 45.0 (.19)[b] | 44.9 (.16)[b] | 44.2 (.26)[e] | 44.7 (.18)[c] | 45.2 (.18)[f,d] |
| n | 774 | 790 | 260 | 135 | 622 | 1060 | 200 | 615 | 925 |
| Ham Minolta b | 4.18 (.10)[c,e] | 4.49 (.10)[d,a] | 4.79 (.14)[f,b] | 4.05 (.19) | 4.28 (.11) | 4.40 (.10) | 3.63 (.15)[e] | 4.31 (.10)[e,f] | 4.70 (.10)[f] |
| n | 459 | 504 | 175 | 75 | 376 | 656 | 128 | 373 | 554 |
| Loin Minolta b | 3.34 (.05) | 3.43 (.06) | 3.49 (.08) | 3.45 (.10) | 3.42 (.06) | 3.34 (0.5) | 3.15 (.08)[e] | 3.31 (.06)[c] | 3.49 (.06)[f,d] |
| n | 765 | 777 | 256 | 131 | 610 | 1050 | 198 | 609 | 906 |

Least squares means were estimated for each substitution site individually are presented with standard errors of the estimates in parenthesis. Significant differences between least squares mean estimates (within a trait and substitution site) are indicated with 2-letter subscripts: a–b $p < .05$, c–d $p < .005$, e–f $p < .0005$. An estimate with superscript "a" is significantly different at $p < .05$ from estimate(s) with superscript "b", same for c–d and e–f at their respective significance levels.

TABLE 5

Association results between the genotypes at I199V substitution site of the PRKAG3 gene and meat quality traits within five commercial pig breeds.

| Genotype | Ham pH | | | Ham Minolta L | | | Ham Minolta b | | |
|---|---|---|---|---|---|---|---|---|---|
| | II | IV | VV | II | IV | VV | II | IV | VV |
| Landrace | 5.82 (.05)[a,c] | 5.72 (.01)[b] | 5.68 (.01)[a,d] | 44.3 (1.6)[a] | 47.2 (.48) | 47.8 (.34)[b] | 3.74 (.62) | 4.27 (.18) | 4.57 (.13) |
| n | 6 | 74 | 242 | 6 | 74 | 242 | 6 | 74 | 238 |
| Large White | 5.75 (.05) | 5.70 (.02) | 5.67 (.02) | 44.4 (1.3) | 46.3 (.61) | 45.8 (.53) | 3.23 (.48)[a,c] | 4.38 (.22)[b] | 4.65 (.19)[d] |
| n | 9 | 56 | 109 | 9 | 56 | 111 | 9 | 55 | 109 |
| Berkshire | 5.91 (.03) | 5.89 (.06) | 5.69 (.15) | 42.4 (.65) | 44.8 (1.1) | 45.0 (3.0) | 3.21 (.26) | 4.34 (.50) | 3.20 (1.3) |
| n | 28 | 10 | 1 | 28 | 10 | 1 | 28 | 10 | 1 |
| Duroc | 5.77 (.03)[a,c] | 5.69 (.02)[b] | 5.66 (.02)[d] | 46.0 (.73)[a] | 47.9 (.46)[b] | 47.9 (.53)[b] | 3.29 (.29)[e] | 4.48 (.18)[f] | 4.58 (.21)[f] |
| n | 33 | 88 | 78 | 33 | 88 | 78 | 33 | 87 | 78 |
| Duroc Synthetic | 5.74 (.02)[a] | 5.70 (.01) | 5.67 (.01)[b] | 47.3 (.60)[a] | 48.0 (.39) | 49.0 (.41)[b] | 4.33 (.23)[c] | 4.42 (.15)[c] | 5.16 (.16)[d,f] |
| n | 52 | 148 | 129 | 52 | 148 | 129 | 52 | 147 | 128 |

| Genotype | Loin pH | | | Loin Minolta L | | | Loin Minolta b | | |
|---|---|---|---|---|---|---|---|---|---|
| | II | IV | VV | II | IV | VV | II | IV | VV |
| Landrace | 5.76 (.04)[a] | 5.71 (.01) | 5.69 (.01)[b] | 41.5 (.95)[a] | 44.2 (.31)[b] | 44.2 (.23)[b] | 2.52 (.31) | 2.98 (.09) | 3.04 (.06) |
| n | 11 | 129 | 398 | 11 | 129 | 399 | 9 | 129 | 387 |
| Large White | 5.73 (.03)[a] | 5.69 (.01) | 5.66 (.01)[b] | 44.7 (.71) | 44.6 (.36) | 44.9 (.30) | 3.31 (.23) | 3.05 (.12) | 3.20 (.10) |
| n | 22 | 110 | 224 | 22 | 110 | 224 | 22 | 105 | 217 |
| Berkshire | 5.88 (.02)[a] | 5.80 (.03)[b] | 5.70 (.13) | 44.4 (.46) | 45.6 (.86) | 44.4 (3.2) | 3.49 (.17) | 3.81 (.29) | 2.55 (1.1) |
| n | 55 | 20 | 1 | 56 | 20 | 1 | 56 | 20 | 1 |
| Duroc | 5.75 (.02) | 5.74 (.01) | 5.71 (.02) | 44.8 (.63) | 45.1 (.39) | 45.8 (.45) | 3.15 (.20) | 3.36 (.12) | 3.50 (.14) |
| n | 36 | 104 | 90 | 36 | 103 | 90 | 36 | 103 | 90 |
| Duroc Synthetic | 5.76 (.02)[a,e] | 5.72 (.01)[b,c] | 5.68 (.01)[f,d] | 45.6 (.41)[a] | 45.7 (.24)[c] | 46.8 (.26)[b,d] | 3.36 (.13)[c] | 3.52 (.08)[c] | 3.83 (.08)[d] |
| n | 75 | 251 | 209 | 75 | 253 | 211 | 75 | 252 | 211 |

Least squares means were estimated for the I199V substitution site individually and are presented with standard errors of the estimates in parenthesis. Significant differences (within a line and substitution site) are indicated with 2-letter superscripts: a–b $p < .05$, c–d $p < .005$, e–f $p < .0005$. An estimate with superscript "a" is significantly different at $p < .05$ from estimate(s) with superscript "b", same for c–d and e–f at their respective significance levels.

TABLE 6

Haplotype frequencies for the T30N, G52S and I199V
substitutions in the PRKAG3 gene in five commercial pig breeds.

| Commercial lines | n | Haplotype[a] frequency | | | | ham pH | loin pH | N[b] ham min L | loin min L | ham min b | loin min b |
|---|---|---|---|---|---|---|---|---|---|---|---|
| | | 1 | 2 | 3 | 4 | | | | | | |
| Landrace | 518 | 0.48 | 0.29 | 0.13 | .10 | 271 | 488 | 284 | 489 | 281 | 475 |
| Large White | 337 | 0.17 | 0.45 | 0.22 | .16 | 151 | 319 | 153 | 319 | 150 | 308 |
| Berkshire | 83 | 0.05 | 0.05 | 0.87 | .03 | 37 | 71 | 37 | 72 | 37 | 72 |
| Duroc | 234 | 0.43 | 0.15 | 0.38 | .04 | 184 | 216 | 184 | 215 | 183 | 215 |
| Duroc Synthetic | 511 | 0.39 | 0.17 | 0.37 | .07 | 299 | 472 | 299 | 474 | 297 | 474 |

[a]haplotype 1: 30N-52G-199V; haplotype 2: 30T-52S-199V; haplotype 3: 30T-52G-199I; haplotype 4: 30T-52G-199V
[b]N — number of animals used in the haplotype association analyses.

EXAMPLE 2

According to the invention, and quite surprisingly, the PRKAG3 alleles were also shown to have a significant association with litter size in animals. The invention in this particular embodiment relates to genetic markers for litter size in animals. It provides a method of screening animals to determine those more likely to produce a larger litter when bred by identifying the presence or absence of a polymorphism in the PRKAG3 gene that is correlated with increased litter size. As used herein, the term "increased litter size" means a biologically significant increase in litter size above the mean of a given population.

An association between PRKAG3 genotype and litter size.

The polymorphism at codon 199 of PRKAG3 was used to genotype sows with litter size data. Two lines were utilized, corresponding to a Landrace line (A) and a Duroc Synthetic line (B) that were previously found to have an association between this polymorphism and meat quality traits.

Data was analyzed according to first parity records and all parities (Table 7).

TABLE 7

| Line | Number of litters Parity 1 | All Parities | Freq allele 1 |
|---|---|---|---|
| A | 224 | 468 | 0.15 |
| B | 311 | 670 | 0.46 |

A statistically significant association (p<0.05) was found between the genotype and litter size traits (Total number born, number born alive) for line B in the First Parity (Table 8). The heterozygote was found to have the largest litter size, in addition the 11 genotype had larger litters than the 22 homozygote (p<0.3) suggesting an advantage for sows carrying at least one copy of allele 1. Interestingly, a similar effect appears to be seen in line A, although the differences in this line do not reach statistical significance, possibly due to the lower numbers of observations. However, the difference between the heterozygote and genotype 22 where there are more observations approaches statistical significance (p<0.1) for number born alive.

Similar effects are seen across the all parities dataset for both lines. In this case the effect in Line A for total number born has a genotype significance of p<0.08.

TABLE 8

Analysis of reproduction traits

| Trait | No of litters LSmeans (s.e.) | | | Genotype p |
|---|---|---|---|---|
| | 1 | 2 | 22 | |
| Line A 1st Parity | | 3 | 164 | |
| NBA | 1.10(1.4) | 1.05(0.63)c | 10.06(0.47)d | 0.21 |
| TNB | 2.25(1.5) | 1.78(0.68)a | 10.89(0.51)b | 0.29 |
| Line B 1st Parity | 6 | 54 | 91 | |
| NBA | .04(0.43)a | .43(0.34)g | 7.34(0.39)b,h | 0.02 |
| TNB | .35(0.47)a | .76(0.38)i | 8.55(0.43)b,j | 0.02 |
| Line A All Parities | 3 | 11 | 344 | |
| NBA | 1.44(1.09)a | 0.64(0.46)a | 10.01(0.34)b | 0.16 |
| TNB | (2.791.16)a,c | 1.42(0.49)b | 10.73(0.37)a,d | 0.08 |
| Line B All Parities | 40 | 24 | 206 | |
| NBA | .66(0.37)a | .13(0.31)b,c | 8.65(0.34)d | 0.13 |
| TNB | .53(0.39)a | 0.02(0.33)b | 9.57(0.36)a | 0.18 |

LSmeans significance levels:
a–b p < 0.30; c–d p < 0.10; e–f p < 0.05; g–h p < 0.01; i–j p < 0.005.

PCR TEST PROTOCALS:

PRKAG3-30 PCR-RFLP Test
StyI polymorphism

Primers
```
                                          (SEQ ID NO:13)
RF1   - 5'ATG AGC TTC CTA GAG CAA GGA G 3'
                                          (SEQ ID NO:13)
RN52R2 - 5'GGC TGC ATG ATG TTA TGT GCC T 3'
```

PCR conditions
Mix1

| 10× PCR buffer | 1.0 µl |
|---|---|
| MgCl$_2$ (15 mM) | 1.0 µl |
| dNTPs (2 mM) | 1.0 µl |

```
            -continued
    Rf1 primer           0.25 µl

RN52R2 primer        0.25 µl

Taq polymerase       0.07 µl ddH2O                5.43 µl genomic DNA          1 µl
```

Combine the Mix1 and DNA in a reaction tube. Overlay with mineral oil. Run the following PCR program: 94° C. for 4 min.; 35 cycles of 94° C. for 45 sec., 59° C. for 45 sec. and 72° C. for 45 sec.; followed by a final extension at 72° C. for 12 min.

Check 3 µl of the PCR on a 2% agarose gel to confirm amplification success and the clean of the negative control. Product size is 270 bp.

Digestion can be performed by the following procedure:

| StyI digestion reaction | |
|---|---|
| PCR product | 3 µl |
| NE Buffer 3 | 1 µl |
| BSA (10 mg/ml) | 0.1 µl |
| StyI (10 U/µl) | 0.3 µl |
| ddH2O | 5.6 µl |

Make a cocktail of PCR product, buffer, enzyme and water. Incubate for 2 hours at 37° C. Mix the digested product with loading dye (1:6) and run on a 4% agarose gel.

```
Genotypes:

11 - 198 and 72 bp               -AAC/AAC

12 - 198, 181, 72 and 17bp       -AAC/ACC

22 - 181, 72 and 17bp            -ACC/ACC

PRKAG3-SINE (Short INterspersed Element)
polymorphism test

Primers
                                        (SEQ ID NO:15)
RP1F -5'GAA ACT CTT CTC CCC ACA GAC 3'
                                        (SEQ ID NO:14)
RN52R2 -5'GGC TGC ATG ATG TTA TGT GCC T 3'

PCR conditions
    Mix1

10× PCR buffer       1.0 µl

MgCl2 (15 mM)        1.0 µl dNTPs (2 mM)         1.0 µl

RP1F primer          0.25 µl

R52R2 primer         0.25 µl

Taq polymerase       0.07 µl ddH2O                5.43 µl genomic DNA          1 µl
```

Combine the Mix1 and DNA in a reaction tube. Overlay with mineral oil. Run the following PCR program:

```
1 cycle of              95° C. for 4 min.;
15 cycles of            95° C. for 1'20"
                        64° C. for 1'
                        74° C. for 1'40"
30 cycles of            95° C. for 1'20"
                        58° C. for 1'
                        73° C. for 1'40"
final extension at      73° C. for 12 min.
```

```
PRKAG3-52 PCR-RFLP Test
HphI polymorphism

Primers
                                        (SEQ ID NO:13)
RF1 - 5'ATG AGC TTC CTA GAG CAA GGA G 3'
                                        (SEQ ID NO:14)
RN52R2 - 5'GGC TGC ATG ATG TTA TGT GCC T 3'

PCR conditions
    Mix1

10× PCR buffer           1.0 µl

MgCl2 (15 mM)            1.0 µl dNTPs (2 mM)             1.0 µl

Rf1 primer (10 mp/µl)    0.25 µl

RN52R2 primer (10 pM/µl) 0.25 µl

Taq polymerase (5 U/µl)  0.07 µl ddH2O                    5.43 µl genomic DNA              1 µl
```

Combine the Mix1 and DNA in a reaction tube. Overlay with mineral oil. Run the following PCR program: 94° C. for 4 min.; 35 cycles of 94° C. for 45 sec., 59° C. for 45 sec. and 72° C. for 45 sec; followed by a final extension at 72° C. for 12 min.

Check 3 µl of the PCR on a 2% agarose gel to confirm amplification success and the clean of the negative control. Product size is 270 bp.

Digestion can be performed by the following procedure:

| HphI digestion reaction | |
|---|---|
| PCR product | 3 µl |
| NE Buffer 4 | 1 µl |
| HphI (5U/µl) | 0.6 µl |
| ddH2O | 5.4 µl |

Make a cocktail of PCR product, buffer, enzyme and water. Incubate for 2 hours at 37° C. Mix the digested product with loading dye (1:6) and run on a 4% agarose gel.

Genotypes:

11—270 bp
12—270 bp, 158 bp and 112 bp
22—158 bp and 112 bp.

PRKAG3-199 PCR-RFLP Test
BsaHI polymorphism

Primers (SEQ ID NO:16)
RNF - 5'GGA GCA AAT GTG CAG ACA AG 3'
(SEQ ID NO:17)
RNR - 5'CCC ACG AAG CTC TGC TTC TT 3'

PCR conditions
Mix1

| | |
|---|---|
| 10× PCR buffer | 1.0 µl |
| MgCl₂ (15 mM) | 1.0 µl |
| dNTPs (2 mM) | 1.0 µl |
| RNF primer (10 pm/µl) | 0.25 µl |
| RFR primer (10 pM/µl) | 0.25 µl |
| Taq polymerase (5 U/µl) | 0.07 µl |
| ddH₂O 5.43 µl | |
| genomic DNA | 1 µl |

Combine the Mix1 and DNA in a reaction tube. Overlay with mineral oil. Run the following PCR program: 94° C. for 4 min.; 35 cycles of 94° C. for 45 sec., 61° C. for 45 sec. and 72° C. for 1 min; followed by a final extension at 72° C. for 12 min.

Check 3 µl of the PCR on a 2% agarose gel to confirm amplification success and the clean of the negative control. Product size is 258 bp.

Digestion can be performed by the following procedure:

| BsaHi digestion reaction | |
|---|---|
| PCR product | 3 µl |
| NE Buffer 4 | 1 µl |
| BasHI (5 U/µl) | 0.6 µl |
| BSA (10 mg/ml) | 0.1 µl |
| ddH₂O | 5.3 µl |

Make a cocktail of PCR product, buffer, enzyme and water. Incubate for 2 hours at 37° C. Mix the digested product with loading dye (1:6) and run on a 4% agarose gel.

Genotypes:

11—167 bp and 91 bp
12—167 bp, 119 bp and 91 bp
22—119 bp and 91 bp

---

What is claimed is:

1. A method for identifying a pig with an increased likelihood of having a phenotype which includes higher ham and join pH and lower ham and loin Minolta, wherein a pig with a cytosine at position 89 of SEQ ID NO: 3 is indicative of said pig being more likely to have the phenotype than a pig with an adenosine at position 89 of SEQ ID NO: 3, said method comprising:

detecting the nucleotide present at position 89 of SEQ ID NO: 3, and relating the nucleotide to the phenotype.

2. The method of claim 1 wherein the nucleotide is detected at position 89 of a PCR sequence using a forward primer and a reverse primer.

3. The method of claim 1 wherein the step of detecting the nucleotide is a method employing allele specific primers.

4. The method of claim 2 wherein said forward primer has an oligonucleitide sequence 5'ATG AGC TTC CTA GAG CAA GGA G 3' (SEQ ID NO:13) and said reverse primer has an oligonucleitide sequence 5'GGC TGC ATG ATG TTA TGT GCC T 3' (SEQ ID NO:14).

5. The method of claim 1 wherein the step of detecting the nucleotide is selected from the group consisting of restriction fragment length polymorphism (RFLP) analysis, heteroduplex analysis, single strand conformational polymorphism (SSCP) analysis, denaturing gradient gel electrophoresis (DGGE), and temperature gradient gel electrophoresis (TGGE).

6. The method of claim 5 further comprising the step of amplifying SEQ ID NO:3 or a region of thereof containing said nucleotide.

7. The method of claim 6 further comprising the step of digesting the amplified region with the restriction endonuclease StyI.

8. The method of claim 7, wherein restriction fragments of 198 and 72 base pairs indicate the presence of an adenosine nucleotide at position 89 of SEQ ID NO: 3.

9. The method of claim 7, wherein restriction fragments of 198, 181, 72, and 17 base pairs indicate the presence of the both an adenosine nucleotide and a cytosine nucleotide at position 89 of SEQ ID NO: 3.

10. The method of claim 7, wherein restriction fragments of 181, 72, and 17 base pairs indicate the presence of a cytosine nucleotide at position 89 of SEQ ID NO: 3.

11. A method for identifying a pig with an increased likelihood of having a phenotype which includes higher ham and loin pH and lower ham and loin Minolta, wherein a pig with an adenosine at position 595 of SEQ ID NO: 3 is indicative of said pig being more likely to have the phenotype than a pig with guanine at position 595 of SEQ ID NO: 3, said method comprising:

detecting the nucleotide present at position 595 of SEQ ID NO: 3, and relating the nucleotide to the phenotype.

12. The method of claim 11 wherein the nucleotide is detected at position 595 of a PCR sequence using a forward primer and a reverse primer.

13. The method of claim 11 wherein the step of detecting the nucleotide is a method employing allele specific primers.

14. The method of claim 12 wherein said forward primer has an oligonucleotide sequence 5'GGA GCA AAT GTG CAG ACA AG 3' (SEQ ID NO:16) and said reverse primer has an oligonucleotide sequence 5'CCC ACG AAG CTC TGC TTC TT 3' (SEQ ID NO:17).

15. The method of claim 11 wherein the step of detecting the nucleotide is selected from the group consisting of restriction fragment length polymorphism (RFLP) analysis, heteroduplex analysis, single strand conformational polymorphism (SSCP) analysis, denaturing gradient gel electrophoresis (DGGE), and temperature gradient gel electrophoresis (TGGE).

16. The method of claim 15 further comprising the step of amplifying SEQ ID NO:3 or a region of thereof containing said nucleotide.

17. The method of claim 16 further comprising the step of digesting the amplified region with the restriction endornuclease BsaHi.

18. The method of claim 17, wherein restriction fragments of 167 and 91 base pairs indicate the presence of an adenosine nucleotide at position 595 of SEQ ID NO: 3.

19. The method of claim 17, wherein restriction fragements of 167, 119, and 91 base pairs indicate the presence of the both an adenosine nucleotide and a guanine nucleotide at position 595 of SEQ ID NO: 3.

20. The method of claim 17, wherein restriction fragments of 119 and 91 base pairs indicate the presence of a guanine nucleotide at position 595 of SEQ ID NO: 3.

21. A method for identifying a pig with an increased likelihood of having a phenotype which includes higher ham and loin pH and lower ham and loin Minolta, wherein a pig with an adenosine at position 595 and codon encoding ARG at positions 598–600 of SEQ ID NO: 3 is indicative of said pig being more likely to have the phenotype than a pig a pig not having this combination of nucleotides present at the recited positions, said method comprising:

detecting the nucleotide present at position 595 of SEQ ID NO: 3, detecting the codon present at nucleotides 598–600 of SEQ ID NO: 3, and relating the nucleotides to the phenotype.

22. A method for identifying a pig with an increased likelihood of having a phenotype which includes higher ham and loin pH and lower ham and loin Minolta, wherein a pig with an cytosine at position 89, guanine at position 154, adenosine at position 595 and codon encoding ARG at positions 598–600, wherein all of the nucleotide positions are from SEQ ID NO: 3, is indicative of said pig being more likely to have the phenotype than a pig not having this combination of nucleotides present at the recited positions, said method comprising:

detecting the nucleotide present at position 89 of SEQ ID NO: 3, detecting the nucleotide present at position 154 of SEQ ID NO: 3, detecting the nucleotide present at position 595 of SEQ ID NO: 3, detecting the codon present at nucleotides 598–600 of SEQ ID NO: 3, and relating the nucleotides to the phenotype.

23. A method for identifying a pig with an increased likelihood of having a phenotype which includes higher ham and loin pH and lower ham and loin Minolta, wherein a pig with an cytosine at position 89, guanine at position 154, and adenosirne at position 595, wherein all of the nucleotide positions are from SEQ ID NO: 3, is indicative of said pig being more likely to have the phenotype than a pig not having this combination of nucleotides present at the recited positions, said method comprising:

detecting the nucleotide present at position 89 of SEQ ID NO: 3, detecting the nucleotide present at position 154 of SEQ ID NO: 3, detecting the nucleotide present at position 595 of SEQ ID NO: 3, and relating the nucleotides to the phenotype.

* * * * *

UNITED STATES PATENT AND TRADEMARK OFFICE
CERTIFICATE OF CORRECTION

PATENT NO. : 6,919,177 B2
DATED : July 19, 2005
INVENTOR(S) : Rothschild et al.

It is certified that error appears in the above-identified patent and that said Letters Patent is hereby corrected as shown below:

Column 75,
Line 4, should read
-- and loin pH and lower ham and loin Minolta, wherein a pig --.

Column 76,
Line 22, should read
-- pig being more likely to have the phenotype than a pig --.

Signed and Sealed this

Fourth Day of October, 2005

JON W. DUDAS
*Director of the United States Patent and Trademark Office*